United States Patent
Stokes et al.

(10) Patent No.: US 6,567,705 B1
(45) Date of Patent: May 20, 2003

(54) SYSTEM AND METHOD FOR ENHANCING CARDIAC SIGNAL SENSING BY CARDIAC PACEMAKERS THROUGH GENETIC TREATMENT

(75) Inventors: Kenneth B. Stokes, Anoka, MN (US); Josée Morissette, Blaine, MN (US)

(73) Assignee: Medtronic, Inc, Minneapolis, MN (US)

(*) Notice: Subject to any disclaimer, the term of this patent is extended or adjusted under 35 U.S.C. 154(b) by 205 days.

(21) Appl. No.: 09/514,907

(22) Filed: Feb. 28, 2000

Related U.S. Application Data

(63) Continuation of application No. 08/682,433, filed on Jul. 17, 1996, now abandoned.

(51) Int. Cl.[7] ................................................ A61N 1/05
(52) U.S. Cl. ..................................................... 607/120
(58) Field of Search ................................. 607/119, 120, 607/122

(56) References Cited

U.S. PATENT DOCUMENTS

| | | | |
|---|---|---|---|
| 4,146,029 A | * 3/1979 | Ellinwood, Jr. | 607/120 |
| 4,360,031 A | 11/1982 | White | 128/786 |
| 4,539,991 A | 9/1985 | Boute | 128/419 |
| 4,554,921 A | 11/1985 | Boute | 128/429 |
| 4,711,251 A | 12/1987 | Stokes | 128/784 |
| 4,920,965 A | 5/1990 | Funke | 128/419 |
| 5,030,204 A | 7/1991 | Badger | 604/95 |
| 5,041,107 A | 8/1991 | Heil | 604/891.1 |
| 5,060,660 A | 10/1991 | Gambale | 128/772 |
| 5,087,243 A | 2/1992 | Boaz | 604/20 |
| 5,104,393 A | 4/1992 | Isner | 606/15 |
| 5,172,694 A | 12/1992 | Flammang | 128/642 |
| 5,174,999 A | 12/1992 | Magruder et al. | 424/423 |
| 5,176,641 A | 1/1993 | Idriss | 604/133 |
| 5,220,917 A | 6/1993 | Cammilli et al. | 128/419 |
| 5,328,470 A | 7/1994 | Nabel et al. | 604/101 |
| 5,380,836 A | 1/1995 | Rogart | 536/23.5 |
| 5,405,376 A | 4/1995 | Mulier et al. | 607/127 |
| 5,433,450 A | 8/1995 | Kratoska | 604/141 |
| 5,447,533 A | * 9/1995 | Vachon et al. | 607/120 |
| 5,458,631 A | 10/1995 | Xavier | 607/117 |
| 5,496,360 A | 3/1996 | Hoffmann | 607/120 |

FOREIGN PATENT DOCUMENTS

| | | | |
|---|---|---|---|
| WO | WO 93/04724 | 3/1993 | |
| WO | WO 94/11506 | 5/1994 | |
| WO | WO 95/05781 | 3/1995 | |
| WO | 90/09391 | 8/2001 | C07H/15/12 |

OTHER PUBLICATIONS

Acsadi, et al., *The New Biol.*, 1991, 3, 71–81.
Barr, et al., *Gene Ther.*, 1994, 1, 51–58.
Chomczynsky, et al., *Anal. Biochem.*, 1997, 162, 156–159.
Duff, et al., *Mol. Pharmacol.*, 1992, 42, 570–574.
Fozzard, et al., *Circ. Res.*, 1985, 56, 475–485.
French, et al., *Circulation*, 1994, 90, 2414–2424.
Gal, et al., *Lab. Invest.*, 1993, 68, 18–25.
Gellens, et al., *Proc. Natl. Acad. Sci. USA*, 1992, 89, 554–558.

(List continued on next page.)

*Primary Examiner*—Jeffrey R. Jastrzab
(74) *Attorney, Agent, or Firm*—Kenneth J. Collier; Thomas Woods

(57) ABSTRACT

Delivery systems for and methods of delivering ion channel protein genetic material to cardiac cells in areas adjacent to where an electrode is to be positioned in a patient's heart to improve or correct the signal to noise ratio of cardiac signals, such as the P-wave, is described herein. More specifically, there is provided a system and method for delivering sodium ion channel proteins or nucleic acid molecules encoding sodium ion channel proteins to a site in the heart adjacent to an electrode to increase the expression of the same, thereby enhancing the cardiac signal amplitude and enabling improved sensing of cardiac signals by an implanted pacemaker.

33 Claims, 5 Drawing Sheets

OTHER PUBLICATIONS

Gluzman, et al., in *Eukaryotic Viral Vectors*, Gluzman, ed., Cold Spring Harbor Press, 1982, pp.187–192.
Johns, *J. Clin. Invest.*, 1995, 96,1152–1158.
Kawakami, et al., *J. Biochem.*, 1986, 100, 389–397.
Kawakami, et al., *Nuc. Acids Res.*, 1986, 14, 2833–2844.
Kallen, et al., *Neuron*, 1990, 4, 233–242.
Kriegler, M. "Gene Transfer and Expression, a Laboratory Manual", W.H. Freeman Co., New York (1990).
Murry, E.J. e.d. "Methods in Molecular Biology", vol. 7, Humana Press, Inc., Clifton, New Jersey (1991).
Parmacek, et al., *J. Biol. Chem.*, 1990, 265, 15970–15976.
Parmacek, et al., *Mol. Cell Biol.*, 1992, 12, 1967–1976.
Sambrook et al., *Molecular Cloning: A Laboratory Manual*, Second Ed. Cold Spring Harbor Press (1989), pp. 7.26–7.29.
Sambrook et al., *Molecular Cloning: A Laboratory Manual*, Second Ed. Cold Spring Harbor Press (1989), pp. 16.1–16.55.
Taouis, et al., *J. Clin. Invest.*, 1991, 88, 375–378.
White, et al., *Mol. Pharmacol.*, 1991, 39, 604–608.
PCT International Search Report dated Jun. 12, 1997, 1 page.
Nabel et al., "Recombinant Gene Expression in Vivo Within Edothelial Cells of the Arterial Wall", *Science*, 1989, 244, 1342–1344.
Aoyagi, et al., J. Biol. Chem. 1993, 268, 27176–27179.
Argentin, et al., Mol. And Cell. Biol. 1994, 14, 777–790.
Cribbs, et al., FEBS 1990, 275, 195–200.
Friedmann and Felgner, Scientific American 1997, Jun., 96–106.
Kanter, et al., Circulation Research 1992, 70, 438–444.
Kass–Eisler, et al., Proc. Natl. Acad. Sci USA 1993, 90, 11498–11502.
Kitsis, R., Proc. Natl. Acad. Sci USA 88, 4138–4142.
Lesage, et al., FEBS 1992, 301, 168–172.
Makita, et al., J. Biol. Chem. 1994, 269, 7571–7578.
Marshall, et al., Science 1995, 269, 1050–1055.
Nabel, et al., Human Gene Therapy 1992, 649–656.
Nabel, et al., Science (1989) 244, 1342–1344.
Nakasaki, J. Biochem 1993, 114, 528–534.
Navankasattusas, et al., Mol. And Cell. Biol. 1994, 14, 7331–7339.
PCT/ISA210, PCT International Search Report.
Plank, et al., J. Biol. Chem. 1994, 269, 12918–12924.
Rogart, Proc. Natl. Acad. Sci. USA 1989, 86, 8170–8174.
Salvatori, et al., Human Gene Therapy 1993, 4, 713–723.
Satin, et al., J. Membrane Biol. 1992, 130, 11–22.
Satin, et al., Scienc 1992, 256, 1202–1205.
Smith, et al., Biochimica et Biophysica Acta 1993, 1174, 63–71.
Tanka et al., Cell Transplantation 1994, 3, S55–S56.
Wang, et al., Am. J. Hum. Genet. 1993, 52, 1074–1084.
Xu, et al., Nucleic Acids Research 1992, 20, 6425–6426.
Zhou, et al., J. Biol. Chem. 1994, 269, 18563–18571.

* cited by examiner

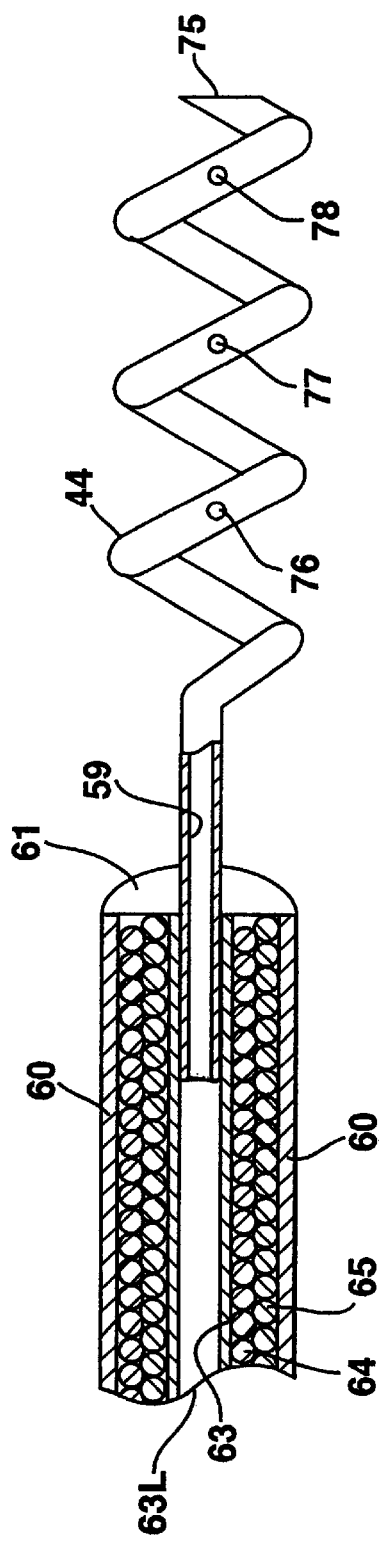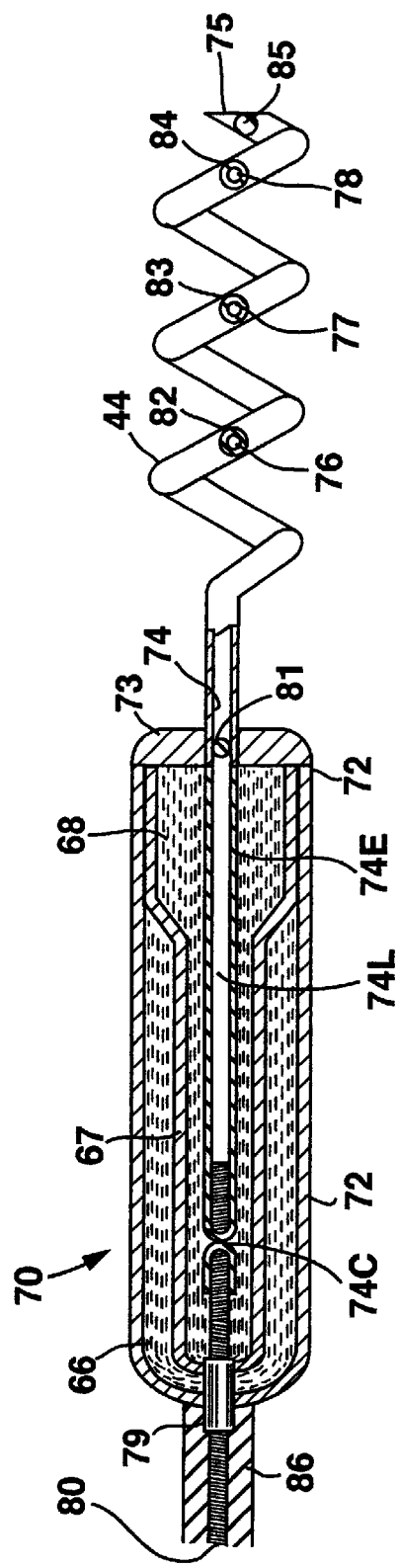

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 6048 bases
      (B) TYPE: nucleic acid
      (C) STRANDEDNESS: double
      (D) TOPOLOGY: linear (xi) SEQUENCE DESCRIPTION: SEQ ID NO: 1:

```
ATG GCA AAC TTC CTA TTA CCT CGG GGC ACC AGC AGC TTC CGC AGG         45
Met Ala Asn Phe Leu Leu Pro Arg Gly Thr Ser Ser Phe Arg Arg
```

```
                           -continued 1                    5                   10                  15

TTC ACA CGG GAG TCC CTG GCA GCC ATC GAG AAG CGC ATG GCG GAG        90
Phe Thr Arg Glu Ser Leu Ala Ala Ile Glu Lys Arg Met Ala Glu
                     20                  25                  30

AAG CAA GCC CGC GGC TCA ACC ACC TTG CAG GAG AGC CGA GAG GGG       135
Lys Gln Ala Arg Gly Ser Thr Thr Leu Gln Glu Ser Arg Glu Gly
                     35                  40                  45

CTG CCC GAG GAG GAG GCT CCC CGG CCC CAG CTG GAC CTG CAG GCC       180
Leu Pro Glu Glu Glu Ala Pro Arg Pro Gln Leu Asp Leu Gln Ala
                     50                  55                  60

TCC AAA AAG CTG CCA GAT CTC TAT GGC AAT CCA CCC CAA GAG CTC       225
Ser Lys Lys Leu Pro Asp Leu Tyr Gly Asn Pro Pro Gln Glu Leu
                     65                  70                  75

ATC GGA GAG CCC CTG GAG GAC CTG GAC CCC TTC TAT AGC ACC CAA       270
Ile Gly Glu Pro Leu Glu Asp Leu Asp Pro Phe Tyr Ser Thr Gln
                     80                  85                  90

AAG ACT TTC ATC GTA CTG AAT AAA GGC AAG ACC ATC TTC CGG TTC       315
Lys Thr Phe Ile Val Leu Asn Lys Gly Lys Thr Ile Phe Arg Phe
                     95                  100                 105

AGT GCC ACC AAC GCC TTG TAT GTC CTC AGT CCC TTC CAC CCA GTT       360
Ser Ala Thr Asn Ala Leu Tyr Val Leu Ser Pro Phe His Pro Val
                     110                 115                 120

CGG AGA GCG GCT GTG AAG ATT CTG GTT CAC TCG CTC TTC AAC ATG       405
Arg Arg Ala Ala Val Lys Ile Leu Val His Ser Leu Phe Asn Met
                     125                 130                 135

CTC ATC ATG TGC ACC ATC CTC ACC AAC TGC GTG TTC ATG GCC CAG       450
Leu Ile Met Cys Thr Ile Leu Thr Asn Cys Val Phe Met Ala Gln
                     140                 145                 150

CAC GAC CCT CCA CCC TGG ACC AAG TAT GTC GAG TAC ACC TTC ACC       495
His Asp Pro Pro Pro Trp Thr Lys Tyr Val Glu Tyr Thr Phe Thr
                     155                 160                 165

GCC ATT TAC ACC TTT GAG TCT CTG GTC AAG ATT CTG GCT CGA GCT       540
Ala Ile Tyr Thr Phe Glu Ser Leu Val Lys Ile Leu Ala Arg Ala
                     170                 175                 180

TTC TGC CTG CAC GCG TTC ACT TTC CTT CGG GAC CCA TGG AAC TGG       585
Phe Cys Leu His Ala Phe Thr Phe Leu Arg Asp Pro Trp Asn Trp
                     185                 190                 195

CTG GAC TTT AGT GTG ATT ATC ATG GCA TAC ACA ACT GAA TTT GTG       630
Leu Asp Phe Ser Val Ile Ile Met Ala Tyr Thr Thr Glu Phe Val
                     200                 205                 210

GAC CTG GGC AAT GTC TCA GCC TTA CGC ACC TTC CGA GTC CTC CGG       675
Asp Leu Gly Asn Val Ser Ala Leu Arg Thr Phe Arg Val Leu Arg
                     215                 220                 225

GCC CTG AAA ACT ATA TCA GTC ATT TCA GGG CTG AAG ACC ATC GTG       720
Ala Leu Lys Thr Ile Ser Val Ile Ser Gly Leu Lys Thr Ile Val
                     230                 235                 240

GGG GCC CTG ATC CAG TCT GTG AAG AAG CTG GCT GAT GTG ATG GTC       765
Gly Ala Leu Ile Gln Ser Val Lys Lys Leu Ala Asp Val Met Val
                     245                 250                 255

CTC ACA GTC TTC TGC CTC AGC GTC TTT GCC CTC ATC GGC CTG CAG       810
Leu Thr Val Phe Cys Leu Ser Val Phe Ala Leu Ile Gly Leu Gln
                     260                 265                 270

CTC TTC ATG GGC AAC CTA AGG CAC AAG TGT GTG CGC AAC TTC ACA       855
Leu Phe Met Gly Asn Leu Arg His Lys Cys Val Arg Asn Phe Thr
                     275                 280                 285

GCG CTC AAC GGC ACC AAC GGC TCC GTG GAG GCC GAC GGC TTG GTC       900
Ala Leu Asn Gly Thr Asn Gly Ser Val Glu Ala Asp Gly Leu Val
                     290                 295                 300

TGG GAA TCC CTG GAC CTT TAC CTC AGT GAT CCA GAA AAT TAC CTG       945
```

```
                                                                    -continued Trp Glu Ser Leu Asp Leu Tyr Leu Ser Asp Pro Glu Asn Tyr Leu
        305                 310                 315

CTC AAG AAC GGC ACC TCT GAT GTG TTA CTG TGT GGG AAC AGC TCT          990
Leu Lys Asn Gly Thr Ser Asp Val Leu Leu Cys Gly Asn Ser Ser
        320                 325                 330

GAC GCT GGG ACA TGT CCG GAG GGC TAC CGG TGC CTA AAG GCA GGC         1035
Asp Ala Gly Thr Cys Pro Glu Gly Tyr Arg Cys Leu Lys Ala Gly
        335                 340                 345

GAG AAC CCC GAC CAC GGC TAC ACC AGC TTC GAT TCC TTT GCC TGG         1080
Glu Asn Pro Asp His Gly Tyr Thr Ser Phe Asp Ser Phe Ala Trp
        350                 355                 360

GCC TTT CTT GCA CTC TTC CGC CTG ATG ACG CAG GAC TGC TGG GAG         1125
Ala Phe Leu Ala Leu Phe Arg Leu Met Thr Gln Asp Cys Trp Glu
        365                 370                 375

CGC CTC TAT CAG CAG ACC CTC AGG TCC GCA GGG AAG ATC TAC ATG         1170
Arg Leu Tyr Gln Gln Thr Leu Arg Ser Ala Gly Lys Ile Tyr Met
        380                 385                 390

ATC TTC TTC ATG CTT GTC ATC TTC CTG GGG TCC TTC TAC CTG GTG         1215
Ile Phe Phe Met Leu Val Ile Phe Leu Gly Ser Phe Tyr Leu Val
        395                 400                 405

AAC CTG ATC CTG GCC GTG GTC GCA ATG GCC TAT GAG GAG CAA AAC         1260
Asn Leu Ile Leu Ala Val Val Ala Met Ala Tyr Glu Glu Gln Asn
        410                 415                 420

CAA GCC ACC ATC GCT GAG ACC GAG GAG AAG GAA AAG CGC TTC CAG         1305
Gln Ala Thr Ile Ala Glu Thr Glu Glu Lys Glu Lys Arg Phe Gln
        425                 430                 435

GAG GCC ATG GAA ATG CTC AAG AAA GAA CAC GAG GCC CTC ACC ATC         1350
Glu Ala Met Glu Met Leu Lys Lys Glu His Glu Ala Leu Thr Ile
        440                 445                 450

AGG GGT GTG GAT ACC GTG TCC CGT AGC TCC TTG GAG ATG TCC CCT         1395
Arg Gly Val Asp Thr Val Ser Arg Ser Ser Leu Glu Met Ser Pro
        455                 460                 465

TTG GCC CCA GTA AAC AGC CAT GAG AGA AGA AGC AAG AGG AGA AAA         1440
Leu Ala Pro Val Asn Ser His Glu Arg Arg Ser Lys Arg Arg Lys
        470                 475                 480

CGG ATG TCT TCA GGA ACT GAG GAG TGT GGG GAG GAC AGG CTC CCC         1485
Arg Met Ser Ser Gly Thr Glu Glu Cys Gly Glu Asp Arg Leu Pro
        485                 490                 495

AAG TCT GAC TCA GAA GAT GGT CCC AGA GCA ATG AAT CAT CTC AGC         1530
Lys Ser Asp Ser Glu Asp Gly Pro Arg Ala Met Asn His Leu Ser
        500                 505                 510

CTC ACC CGT GGC CTC AGC AGG ACT TCT ATG AAG CCA CGT TCC AGC         1575
Leu Thr Arg Gly Leu Ser Arg Thr Ser Met Lys Pro Arg Ser Ser
        515                 520                 525

CGC GGG AGC ATT TTC ACC TTT CGC AGG CGA GAC CTG GGT TCT GAA         1620
Arg Gly Ser Ile Phe Thr Phe Arg Arg Arg Asp Leu Gly Ser Glu
        530                 535                 540

GCA GAT TTT GCA GAT GAT GAA AAC AGC ACA GCG CGG GAG AGC GAG         1665
Ala Asp Phe Ala Asp Asp Glu Asn Ser Thr Ala Arg Glu Ser Glu
        545                 550                 555

AGC CAC CAC ACA TCA CTG CTG GTG CCC TGG CCC CTG CGC CGG ACC         1710
Ser His His Thr Ser Leu Leu Val Pro Trp Pro Leu Arg Arg Thr
        560                 565                 570

AGT GCC CAG GGA CAG CCC AGT CCC GGA ACC TCG GCT CCT GGC CAC         1755
Ser Ala Gln Gly Gln Pro Ser Pro Gly Thr Ser Ala Pro Gly His
        575                 580                 585

GCC CTC CAT GGC AAA AAG AAC AGC ACT GTG GAC TGC AAT GGG GTG         1800
Ala Leu His Gly Lys Lys Asn Ser Thr Val Asp Cys Asn Gly Val
        590                 595                 600
```

```
GTC TCA TTA CTG GGG GCA GGC GAC CCA GAG GCC ACA TCC CCA GGA         1845
Val Ser Leu Leu Gly Ala Gly Asp Pro Glu Ala Thr Ser Pro Gly
            605                 610                 615

AGC CAC CTC CTC CGC CCT GTG ATG CTA GAG CAC CCG CCA GAC ACG         1890
Ser His Leu Leu Arg Pro Val Met Leu Glu His Pro Pro Asp Thr
            620                 625                 630

ACC ACG CCA TCG GAG GAG CCA GGC GGC CCC CAG ATG CTG ACC TCC         1935
Thr Thr Pro Ser Glu Glu Pro Gly Gly Pro Gln Met Leu Thr Ser
            635                 640                 645

CAG GCT CCG TGT GTA GAT GGC TTC GAG GAG CCA GGA GCA CGG CAG         1980
Gln Ala Pro Cys Val Asp Gly Phe Glu Glu Pro Gly Ala Arg Gln
            650                 655                 660

CGG GCC CTC AGC GCA GTC AGC GTC CTC ACA AGC GCA CTG GAA GAG         2025
Arg Ala Leu Ser Ala Val Ser Val Leu Thr Ser Ala Leu Glu Glu
            665                 670                 675

TTA GAG GAG TCT CGC CAC AAG TGT CCA CCA TGC TGG AAC CGT CTC         2070
Leu Glu Glu Ser Arg His Lys Cys Pro Pro Cys Trp Asn Arg Leu
            680                 685                 690

GCC CAG CGC TAC CTG ATC TGG GAG TGC TGC CCG CTG TGG ATG TCC         2115
Ala Gln Arg Tyr Leu Ile Trp Glu Cys Cys Pro Leu Trp Met Ser
            695                 700                 705

ATC AAG CAG GGA GTG AAG TTG GTG GTC ATG GAC CCG TTT ACT GAC         2160
Ile Lys Gln Gly Val Lys Leu Val Val Met Asp Pro Phe Thr Asp
            710                 715                 720

CTC ACC ATC ACT ATG TGC ATC GTA CTC AAC ACA CTC TTC ATG GCG         2205
Leu Thr Ile Thr Met Cys Ile Val Leu Asn Thr Leu Phe Met Ala
            725                 730                 735

CTG GAG CAC TAC AAC ATG ACA AGT GAA TTC GAG GAG ATG CTG CAG         2250
Leu Glu His Tyr Asn Met Thr Ser Glu Phe Glu Glu Met Leu Gln
            740                 745                 750

GTC GGA AAC CTG GTC TTC ACA GGG ATT TTC ACA GCA GAG ATG ACC         2295
Val Gly Asn Leu Val Phe Thr Gly Ile Phe Thr Ala Glu Met Thr
            755                 760                 765

TTC AAG ATC ATT GCC CTC GAC CCC TAC TAC TAC TTC CAA CAG GGC         2340
Phe Lys Ile Ile Ala Leu Asp Pro Tyr Tyr Tyr Phe Gln Gln Gly
            770                 775                 780

TGG AAC ATC TTC GAC AGC ATC ATC GTC ATC CTT AGC CTC ATG GAG         2385
Trp Asn Ile Phe Asp Ser Ile Ile Val Ile Leu Ser Leu Met Glu
            785                 790                 795

CTG GGC CTG TCC CGC ATG AGC AAC TTG TCG GTG CTG CGC TCC TTC         2430
Leu Gly Leu Ser Arg Met Ser Asn Leu Ser Val Leu Arg Ser Phe
            800                 805                 810

CGC CTG CTG CGG GTC TTC AAG CTG GCC AAA TCA TGG CCC ACC CTG         2475
Arg Leu Leu Arg Val Phe Lys Leu Ala Lys Ser Trp Pro Thr Leu
            815                 820                 825

AAC ACA CTC ATC AAG ATC ATC GGG AAC TCA GTG GGG GCA CTG GGG         2520
Asn Thr Leu Ile Lys Ile Ile Gly Asn Ser Val Gly Ala Leu Gly
            830                 835                 840

AAC CTG ACA CTG GTG CTA GCC ATC ATC GTG TTC ATC TTT GCT GTG         2565
Asn Leu Thr Leu Val Leu Ala Ile Ile Val Phe Ile Phe Ala Val
            845                 850                 855

GTG GGC ATG CAG CTC TTT GGC AAG AAC TAC TCG GAG CTG AGG GAC         2610
Val Gly Met Gln Leu Phe Gly Lys Asn Tyr Ser Glu Leu Arg Asp
            860                 865                 870

AGC GAC TCA GGC CTG CTG CCT CGC TGG CAC ATG ATG GAC TTC TTT         2655
Ser Asp Ser Gly Leu Leu Pro Arg Trp His Met Met Asp Phe Phe
            875                 880                 885

CAT GCC TTC CTA ATC ATC TTC CGC ATC CTC TGT GGA GAG TGG ATC         2700
His Ala Phe Leu Ile Ile Phe Arg Ile Leu Cys Gly Glu Trp Ile
            890                 895                 900
```

```
-continued

GAG ACC ATG TGG GAC TGC ATG GAG GTG TCG GGG CAG TCA TTA TGC         2745
Glu Thr Met Trp Asp Cys Met Glu Val Ser Gly Gln Ser Leu Cys
                905                 910                 915

CTG CTG GTC TTC TTG CTT GTT ATG GTC ATT GGC AAC CTT GTG GTC         2790
Leu Leu Val Phe Leu Leu Val Met Val Ile Gly Asn Leu Val Val
                920                 925                 930

CTG AAT CTC TTC CTG GCC TTG CTG CTC AGC TCC TTC AGT GCA GAC         2835
Leu Asn Leu Phe Leu Ala Leu Leu Leu Ser Ser Phe Ser Ala Asp
                935                 940                 945

AAC CTC ACA GCC CCT GAT GAG GAC AGA GAG ATG AAC AAC CTC CAG         2880
Asn Leu Thr Ala Pro Asp Glu Asp Arg Glu Met Asn Asn Leu Gln
                950                 955                 960

CTG GCC CTG GCC CGC ATC CAG AGG GGC CTG CGC TTT GTC AAG CGG         2925
Leu Ala Leu Ala Arg Ile Gln Arg Gly Leu Arg Phe Val Lys Arg
                965                 970                 975

ACC ACC TGG GAT TTC TGC TGT GGT CTC CTG CGG CAC CGG CCT CAG         2970
Thr Thr Trp Asp Phe Cys Cys Gly Leu Leu Arg His Arg Pro Gln
                980                 985                 990

AAG CCC GCA GCC CTT GCC GCC CAG GGC CAG CTG CCC AGC TGC ATT         3015
Lys Pro Ala Ala Leu Ala Ala Gln Gly Gln Leu Pro Ser Cys Ile
                995                1000                1005

GCC ACC CCC TAC TCC CCG CCA CCC CCA GAG ACG GAG AAG GTG CCT         3060
Ala Thr Pro Tyr Ser Pro Pro Pro Glu Thr Glu Lys Val Pro
               1010                1015                1020

CCC ACC CGC AAG GAA ACA CAG TTT GAG GAA GGC GAG CAA CCA GGC         3105
Pro Thr Arg Lys Glu Thr Gln Phe Glu Glu Gly Glu Gln Pro Gly
               1025                1030                1035

CAG GGC ACC CCC GGG GAT CCA GAC GCC GTG TGT GTG CCC ATC GCT         3150
Gln Gly Thr Pro Gly Asp Pro Asp Ala Val Cys Val Pro Ile Ala
               1040                1045                1050

GTG GCC GAG TCA GAC ACA GAT GAC CAA GAA GAG GAT GAG GAG AAC         3195
Val Ala Glu Ser Asp Thr Asp Asp Gln Glu Glu Asp Glu Glu Asn
               1055                1060                1065

AGC CTG GGC ACG GAG GAG GAG TCC AGC AAG CAG CAG GAA TCC CAG         3240
Ser Leu Gly Thr Glu Glu Glu Ser Ser Lys Gln Gln Glu Ser Gln
               1070                1075                1080

CCT GTG TCC GGC TGG CCC AGA GGC CCT CCG GAT TCC AGG ACC TGG         3285
Pro Val Ser Gly Trp Pro Arg Gly Pro Pro Asp Ser Arg Thr Trp
               1085                1090                1095

AGC CAG GTG TCA GCG ACT GCC TCC TCT GAG GCC GAG GCC AGT GCA         3330
Ser Gln Val Ser Ala Thr Ala Ser Ser Glu Ala Glu Ala Ser Ala
               1100                1105                1110

TCT CAG GCC GAC TGG CGG CAG CAG TGG AAA GCG GAA CCC CAG GCC         3375
Ser Gln Ala Asp Trp Arg Gln Gln Trp Lys Ala Glu Pro Gln Ala
               1115                1120                1125

CCA GGG TGC GGT GAG ACC CCA GAG GAC AGT TGC TCC GAG GGC AGC         3420
Pro Gly Cys Gly Glu Thr Pro Glu Asp Ser Cys Ser Glu Gly Ser
               1130                1135                1140

ACA GCA GAC ATG ACC AAC ACC GCT GAG CTC CTG GAG CAG ATC CCT         3465
Thr Ala Asp Met Thr Asn Thr Ala Glu Leu Leu Glu Gln Ile Pro
               1145                1150                1155

GAC CTC GGC CAG GAT GTC AAG GAC CCA GAG GAC TGC TTC ACT GAA         3510
Asp Leu Gly Gln Asp Val Lys Asp Pro Glu Asp Cys Phe Thr Glu
               1160                1165                1170

GGC TGT GTC CGG CGC TGT CCC TGC TGT GCG GTG GAC ACC ACA CAG         3555
Gly Cys Val Arg Arg Cys Pro Cys Cys Ala Val Asp Thr Thr Gln
               1175                1180                1185

GCC CCA GGG AAG GTC TGG TGG CGG TTG CGC AAG ACC TGC TAC CAC         3600
Ala Pro Gly Lys Val Trp Trp Arg Leu Arg Lys Thr Cys Tyr His
```

```
                           1190                 1195                 1200
ATC GTG GAG CAC AGC TGG TTC GAG ACA TTC ATC ATC TTC ATG ATC              3645
Ile Val Glu His Ser Trp Phe Glu Thr Phe Ile Ile Phe Met Ile
                  1205                 1210                 1215

CTA CTC AGC AGT GGA GCG CTG GCC TTC GAG GAC ATC TAC CTA GAG              3690
Leu Leu Ser Ser Gly Ala Leu Ala Phe Glu Asp Ile Tyr Leu Glu
                  1220                 1225                 1230

GAG CGG AAG ACC ATC AAG GTT CTG CTT GAG TAT GCC GAC AAG ATG              3735
Glu Arg Lys Thr Ile Lys Val Leu Leu Glu Tyr Ala Asp Lys Met
                  1235                 1240                 1245

TTC ACA TAT GTC TTC GTG CTG GAG ATG CTG CTC AAG TGG GTG GCC              3780
Phe Thr Tyr Val Phe Val Leu Glu Met Leu Leu Lys Trp Val Ala
                  1250                 1255                 1260

TAC GGC TTC AAG AAG TAC TTC ACC AAT GCC TGG TGC TGG CTC GAC              3825
Tyr Gly Phe Lys Lys Tyr Phe Thr Asn Ala Trp Cys Trp Leu Asp
                  1265                 1270                 1275

TTC CTC ATC GTA GAC GTC TCT CTG GTC AGC CTG GTG GCC AAC ACC              3870
Phe Leu Ile Val Asp Val Ser Leu Val Ser Leu Val Ala Asn Thr
                  1280                 1285                 1290

CTG GGC TTT GCC GAG ATG GGC CCC ATC AAG TCA CTG CGG ACG CTG              3915
Leu Gly Phe Ala Glu Met Gly Pro Ile Lys Ser Leu Arg Thr Leu
                  1295                 1300                 1305

CGT GCA CTC CGT CCT CTG AGA GCT CTG TCA CGA TTT GAG GGC ATG              3960
Arg Ala Leu Arg Pro Leu Arg Ala Leu Ser Arg Phe Glu Gly Met
                  1310                 1315                 1320

AGG GTG GTG GTC AAT GCC CTG GTG GGC GCC ATC CCG TCC ATC ATG              4005
Arg Val Val Val Asn Ala Leu Val Gly Ala Ile Pro Ser Ile Met
                  1325                 1330                 1335

AAC GTC CTC CTC GTC TGC CTC ATC TTC TGG CTC ATC TTC AGC ATC              4050
Asn Val Leu Leu Val Cys Leu Ile Phe Trp Leu Ile Phe Ser Ile
                  1340                 1345                 1350

ATG GGC GTG AAC CTC TTT GCG GGG AAG TTT GGG AGG TGC ATC AAC              4095
Met Gly Val Asn Leu Phe Ala Gly Lys Phe Gly Arg Cys Ile Asn
                  1355                 1360                 1365

CAG ACA GAG GGA GAC TTG CCT TTG AAC TAC ACC ATC GTG AAC AAC              4140
Gln Thr Glu Gly Asp Leu Pro Leu Asn Tyr Thr Ile Val Asn Asn
                  1370                 1375                 1380

AAG AGC CAG TGT GAG TCC TTG AAC TTG ACC GGA GAA TTG TAC TGG              4185
Lys Ser Gln Cys Glu Ser Leu Asn Leu Thr Gly Glu Leu Tyr Trp
                  1385                 1390                 1395

ACC AAG GTG AAA GTC AAC TTT GAC AAC GTG GGG GCC GGG TAC CTG              4230
Thr Lys Val Lys Val Asn Phe Asp Asn Val Gly Ala Gly Tyr Leu
                  1400                 1405                 1410

GCC CTT CTG CAG GTG GCA ACA TTT AAA GGC TGG ATG GAC ATT ATG              4275
Ala Leu Leu Gln Val Ala Thr Phe Lys Gly Trp Met Asp Ile Met
                  1415                 1420                 1425

TAT GCA GCT GTG GAC TCC AGG GGG TAT GAA GAG CAG CCT CAG TGG              4320
Tyr Ala Ala Val Asp Ser Arg Gly Tyr Glu Glu Gln Pro Gln Trp
                  1430                 1435                 1440

GAA TAC AAC CTC TAC ATG TAC ATC TAT TTT GTC ATT TTC ATC ATC              4365
Glu Tyr Asn Leu Tyr Met Tyr Ile Tyr Phe Val Ile Phe Ile Ile
                  1445                 1450                 1455

TTT GGG TCT TTC TTC ACC CTG AAC CTC TTT ATT GGT GTC ATC ATT              4410
Phe Gly Ser Phe Phe Thr Leu Asn Leu Phe Ile Gly Val Ile Ile
                  1460                 1465                 1470

GAC AAC TTC AAC CAA CAG AAG AAA AAG TTA GGG GGC CAG GAC ATC              4455
Asp Asn Phe Asn Gln Gln Lys Lys Lys Leu Gly Gly Gln Asp Ile
                  1475                 1480                 1485

TTC ATG ACA GAG GAG CAG AAG AAG TAC TAC AAT GCC ATG AAG AAG              4500
```

-continued

```
                            Phe Met Thr Glu Glu Gln Lys Lys Tyr Tyr Asn Ala Met Lys Lys
                                            1490                1495                1500

CTG GGC TCC AAG AAG CCC CAG AAG CCC ATC CCA CGG CCC CTG AAC              4545
Leu Gly Ser Lys Lys Pro Gln Lys Pro Ile Pro Arg Pro Leu Asn
                1505                1510                1515

AAG TAC CAG GGC TTC ATA TTC GAC ATT GTG ACC AAG CAG GCC TTT              4590
Lys Tyr Gln Gly Phe Ile Phe Asp Ile Val Thr Lys Gln Ala Phe
                1520                1525                1530

GAC GTC ACC ATC ATG TTT CTG ATC TGC TTG AAT ATG GTG ACC ATG              4635
Asp Val Thr Ile Met Phe Leu Ile Cys Leu Asn Met Val Thr Met
                1535                1540                1545

ATG GTG GAG ACA GAT GAC CAA AGT CCT GAG AAA ATC AAC ATC TTG              4680
Met Val Glu Thr Asp Asp Gln Ser Pro Glu Lys Ile Asn Ile Leu
                1550                1555                1560

GCC AAG ATC AAC CTG CTC TTT GTG GCC ATC TTC ACA GGC GAG TGT              4725
Ala Lys Ile Asn Leu Leu Phe Val Ala Ile Phe Thr Gly Glu Cys
                1565                1570                1575

ATT GTC AAG CTG GCT GCC CTG CGC CAC TAC TAC TTC ACC AAC AGC              4770
Ile Val Lys Leu Ala Ala Leu Arg His Tyr Tyr Phe Thr Asn Ser
                1580                1585                1590

TGG AAT ATC TTC GAC TTC GTG GTT GTC ATC CTC TCC ATC GTG GGC              4815
Trp Asn Ile Phe Asp Phe Val Val Val Ile Leu Ser Ile Val Gly
                1595                1600                1605

ACT GTG CTC TCG GAC ATC ATC CAG AAG TAC TTC TTC TCC CCG ACG              4860
Thr Val Leu Ser Asp Ile Ile Gln Lys Tyr Phe Phe Ser Pro Thr
                1610                1615                1620

CTC TTC CGA GTC ATC CGC CTG GCC CGA ATA GGC CGC ATC CTC AGA              4905
Leu Phe Arg Val Ile Arg Leu Ala Arg Ile Gly Arg Ile Leu Arg
                1625                1630                1635

CTG ATC CGA GGG GCC AAG GGG ATC CGC ACG CTG CTC TTT GCC CTC              4950
Leu Ile Arg Gly Ala Lys Gly Ile Arg Thr Leu Leu Phe Ala Leu
                1640                1645                1650

ATG ATG TCC CTG CCT GCC CTC TTC AAC ATC GGG CTG CTG CTC TTC              4995
Met Met Ser Leu Pro Ala Leu Phe Asn Ile Gly Leu Leu Leu Phe
                1655                1660                1665

CTC GTC ATG TTC ATC TAC TCC ATC TTT GGC ATG GCC AAC TTC GCT              5040
Leu Val Met Phe Ile Tyr Ser Ile Phe Gly Met Ala Asn Phe Ala
                1670                1675                1680

TAT GTC AAG TGG GAG GCT GGC ATC GAC GAC ATG TTC AAC TTC CAG              5085
Tyr Val Lys Trp Glu Ala Gly Ile Asp Asp Met Phe Asn Phe Gln
                1685                1690                1695

ACC TTC GCC AAC AGC ATG CTG TGC CTC TTC CAG ATC ACC ACG TCG              5130
Thr Phe Ala Asn Ser Met Leu Cys Leu Phe Gln Ile Thr Thr Ser
                1700                1705                1710

GCC GGC TGG GAT GGC CTC CTC AGC CCC ATC CTC AAC ACT GGG CCG              5175
Ala Gly Trp Asp Gly Leu Leu Ser Pro Ile Leu Asn Thr Gly Pro
                1715                1720                1725

CCC TAC TGC GAC CCC ACT CTG CCC AAC AGC AAT GGC TCT CGG GGG              5220
Pro Tyr Cys Asp Pro Thr Leu Pro Asn Ser Asn Gly Ser Arg Gly
                1730                1735                1740

GAC TGC GGG AGC CCA GCC GTG GGC ATC CTC TTC TTC ACC ACC TAC              5265
Asp Cys Gly Ser Pro Ala Val Gly Ile Leu Phe Phe Thr Thr Tyr
                1745                1750                1755

ATC ATC ATC TCC TTC CTC ATC GTG GTC AAC ATG TAC ATT GCC ATC              5310
Ile Ile Ile Ser Phe Leu Ile Val Val Asn Met Tyr Ile Ala Ile
                1760                1765                1770

ATC CTG GAG AAC TTC AGC GTG GCC ACG GAG GAG AGC ACC GAG CCC              5355
Ile Leu Glu Asn Phe Ser Val Ala Thr Glu Glu Ser Thr Glu Pro
                1775                1780                1785
```

```
CTG AGT GAG GAC GAC TTC GAT ATG TTC TAT GAG ATC TGG GAG AAA              5400
Leu Ser Glu Asp Asp Phe Asp Met Phe Tyr Glu Ile Trp Glu Lys
            1790                1795                1800

TTT GAC CCA GAG GCC ACT CAG TTT ATT GAG TAT TCG GTC CTG TCT              5445
Phe Asp Pro Glu Ala Thr Gln Phe Ile Glu Tyr Ser Val Leu Ser
            1805                1810                1815

GAC TTT GCC GAC GCC CTG TCT GAG CCA CTC CGT ATC GCC AAG CCC              5490
Asp Phe Ala Asp Ala Leu Ser Glu Pro Leu Ile Arg Ala Lys Pro
            1820                1825                1830

AAC CAG ATA AGC CTC ATC AAC ATG GAC CTG CCC ATG GTG AGT GGG              5535
Asn Gln Ile Ser Leu Ile Asn Met Asp Leu Pro Met Val Ser Gly
            1835                1840                1845

GAC CGC ATC CAT TGC ATG GAC ATT CTC TTT GCC TTC ACC AAA AGG              5580
Asp Arg Ile His Cys Met Asp Ile Leu Phe Ala Phe Thr Lys Arg
            1850                1855                1860

GTC CTG GGG GAG TCT GGG GAG ATG GAC GCC CTG AAG ATC CAG ATG              5625
Val Leu Gly Glu Ser Gly Glu Met Asp Ala Leu Lys Ile Gln Met
            1865                1870                1875

GAG GAG AAG TTC ATG GCA GCC AAC CCA TCC AAG ATC TCC TAC GAG              5670
Glu Glu Lys Phe Met Ala Ala Asn Pro Ser Lys Ile Ser Tyr Glu
            1880                1885                1890

CCC ATC ACC ACC ACA CTC CGG CGC AAG CAC GAA GAG GTG TCG GCC              5715
Pro Ile Thr Thr Thr Leu Arg Arg Lys His Glu Glu Val Ser Ala
            1895                1900                1905

ATG GTT ATC CAG AGA GCC TTC CGC AGG CAC CTG CTG CAA CGC TCT              5760
Met Val Ile Gln Arg Ala Phe Arg Arg His Leu Leu Gln Arg Ser
            1910                1915                1920

TTG AAG CAT GCC TCC TTC CTC TTC CGT CAG CAG GCG GGC AGC GGC              5805
Leu Lys His Ala Ser Phe Leu Phe Arg Gln Gln Ala Gly Ser Gly
            1925                1930                1935

CTC TCC GAA GAG GAT GCC CCT GAG CGA GAG GGC CTC ATC GCC TAC              5850
Leu Ser Glu Glu Asp Ala Pro Glu Arg Glu Gly Leu Ile Ala Tyr
            1940                1945                1950

GTG ATG AGT GAG AAC TTC TCC CGA CCC CTT GGC CCA CCC TCC AGC              5895
Val Met Ser Glu Asn Phe Ser Arg Pro Leu Gly Pro Pro Ser Ser
            1955                1960                1965

TCC TCC ATC TCC TCC ACT TCC TTC CCA CCC TCC TAT GAC AGT GTC              5940
Ser Ser Ile Ser Ser Thr Ser Phe Pro Pro Ser Tyr Asp Ser Val
            1970                1975                1980

ACT AGA GCC ACC AGC GAT AAC CTC CAG GTG CGG GGG TCT GAC TAC              5985
Thr Arg Ala Thr Ser Asp Asn Leu Gln Val Arg Gly Ser Asp Tyr
            1985                1990                1995

AGC CAC AGT GAA GAT CTC GCC GAC TTC CCC CCT TCT CCG GAC AGG              6030
Ser His Ser Glu Asp Leu Ala Asp Phe Pro Pro Ser Pro Asp Arg
            2000                2005                2010

GAC CGT GAG TCC ATC GTG                                                  6048
Asp Arg Glu Ser Ile Val
            2015
```

(2) INFORMATION FOR SEQ ID NO: 2:

(i) SEQUENCE CHARACTERISTICS:
        (A) LENGTH: 2016 amino acids
        (B) TYPE: amino acid
        (C) STRANDEDNESS: single
        (D) TOPOLOGY: unknown (xi) SEQUENCE DESCRIPTION: SEQ ID NO: 2:

```
Met Ala Asn Phe Leu Leu Pro Arg Gly Thr Ser Ser Phe Arg Arg
 1               5                  10                  15

Phe Thr Arg Glu Ser Leu Ala Ala Ile Glu Lys Arg Met Ala Glu
```

-continued

```
                20                  25                  30
Lys Gln Ala Arg Gly Ser Thr Thr Leu Gln Glu Ser Arg Glu Gly
                35                  40                  45
Leu Pro Glu Glu Ala Pro Arg Pro Gln Leu Asp Leu Gln Ala
                50                  55                  60
Ser Lys Lys Leu Pro Asp Leu Tyr Gly Asn Pro Pro Gln Glu Leu
                65                  70                  75
Ile Gly Glu Pro Leu Glu Asp Leu Asp Pro Phe Tyr Ser Thr Gln
                80                  85                  90
Lys Thr Phe Ile Val Leu Asn Lys Gly Lys Thr Ile Phe Arg Phe
                95                 100                 105
Ser Ala Thr Asn Ala Leu Tyr Val Leu Ser Pro Phe His Pro Val
               110                 115                 120
Arg Arg Ala Ala Val Lys Ile Leu Val His Ser Leu Phe Asn Met
               125                 130                 135
Leu Ile Met Cys Thr Ile Leu Thr Asn Cys Val Phe Met Ala Gln
               140                 145                 150
His Asp Pro Pro Trp Thr Lys Tyr Val Glu Tyr Thr Phe Thr
               155                 160                 165
Ala Ile Tyr Thr Phe Glu Ser Leu Val Lys Ile Leu Ala Arg Ala
               170                 175                 180
Phe Cys Leu His Ala Phe Thr Phe Leu Arg Asp Pro Trp Asn Trp
               185                 190                 195
Leu Asp Phe Ser Val Ile Ile Met Ala Tyr Thr Thr Glu Phe Val
               200                 205                 210
Asp Leu Gly Asn Val Ser Ala Leu Arg Thr Phe Arg Val Leu Arg
               215                 220                 225
Ala Leu Lys Thr Ile Ser Val Ile Ser Gly Leu Lys Thr Ile Val
               230                 235                 240
Gly Ala Leu Ile Gln Ser Val Lys Lys Leu Ala Asp Val Met Val
               245                 250                 255
Leu Thr Val Phe Cys Leu Ser Val Phe Ala Leu Ile Gly Leu Gln
               260                 265                 270
Leu Phe Met Gly Asn Leu Arg His Lys Cys Val Arg Asn Phe Thr
               275                 280                 285
Ala Leu Asn Gly Thr Asn Gly Ser Val Glu Ala Asp Gly Leu Val
               290                 295                 300
Trp Glu Ser Leu Asp Leu Tyr Leu Ser Asp Pro Glu Asn Tyr Leu
               305                 310                 315
Leu Lys Asn Gly Thr Ser Asp Val Leu Leu Cys Gly Asn Ser Ser
               320                 325                 330
Asp Ala Gly Thr Cys Pro Glu Gly Tyr Arg Cys Leu Lys Ala Gly
               335                 340                 345
Glu Asn Pro Asp His Gly Tyr Thr Ser Phe Asp Ser Phe Ala Trp
               350                 355                 360
Ala Phe Leu Ala Leu Phe Arg Leu Met Thr Gln Asp Cys Trp Glu
               365                 370                 375
Arg Leu Tyr Gln Gln Thr Leu Arg Ser Ala Gly Lys Ile Tyr Met
               380                 385                 390
Ile Phe Phe Met Leu Val Ile Phe Leu Gly Ser Phe Tyr Leu Val
               395                 400                 405
Asn Leu Ile Leu Ala Val Val Ala Met Ala Tyr Glu Glu Gln Asn
               410                 415                 420
```

-continued

```
Gln Ala Thr Ile Ala Glu Thr Glu Glu Lys Glu Lys Arg Phe Gln
            425                 430                 435
Glu Ala Met Glu Met Leu Lys Lys Glu His Glu Ala Leu Thr Ile
            440                 445                 450
Arg Gly Val Asp Thr Val Ser Arg Ser Leu Glu Met Ser Pro
            455                 460                 465
Leu Ala Pro Val Asn Ser His Glu Arg Arg Ser Lys Arg Arg Lys
            470                 475                 480
Arg Met Ser Ser Gly Thr Glu Glu Cys Gly Asp Arg Leu Pro
            485                 490                 495
Lys Ser Asp Ser Glu Asp Gly Pro Arg Ala Met Asn His Leu Ser
            500                 505                 510
Leu Thr Arg Gly Leu Ser Arg Thr Ser Met Lys Pro Arg Ser Ser
            515                 520                 525
Arg Gly Ser Ile Phe Thr Phe Arg Arg Asp Leu Gly Ser Glu
            530                 535                 540
Ala Asp Phe Ala Asp Asp Glu Asn Ser Thr Ala Arg Glu Ser Glu
            545                 550                 555
Ser His His Thr Ser Leu Leu Val Pro Trp Pro Leu Arg Arg Thr
            560                 565                 570
Ser Ala Gln Gly Gln Pro Ser Pro Gly Thr Ser Ala Pro Gly His
            575                 580                 585
Ala Leu His Gly Lys Lys Asn Ser Thr Val Asp Cys Asn Gly Val
            590                 595                 600
Val Ser Leu Leu Gly Ala Gly Asp Pro Glu Ala Thr Ser Pro Gly
            605                 610                 615
Ser His Leu Leu Arg Pro Val Met Leu Glu His Pro Pro Asp Thr
            620                 625                 630
Thr Thr Pro Ser Glu Glu Pro Gly Gly Pro Gln Met Leu Thr Ser
            635                 640                 645
Gln Ala Pro Cys Val Asp Gly Phe Glu Glu Pro Gly Ala Arg Gln
            650                 655                 660
Arg Ala Leu Ser Ala Val Ser Val Leu Thr Ser Ala Leu Glu Glu
            665                 670                 675
Leu Glu Glu Ser Arg His Lys Cys Pro Pro Cys Trp Asn Arg Leu
            680                 685                 690
Ala Gln Arg Tyr Leu Ile Trp Glu Cys Cys Pro Leu Trp Met Ser
            695                 700                 705
Ile Lys Gln Gly Val Lys Leu Val Val Met Asp Pro Phe Thr Asp
            710                 715                 720
Leu Thr Ile Thr Met Cys Ile Val Leu Asn Thr Leu Phe Met Ala
            725                 730                 735
Leu Glu His Tyr Asn Met Thr Ser Glu Phe Glu Met Leu Gln
            740                 745                 750
Val Gly Asn Leu Val Phe Thr Gly Ile Phe Thr Ala Glu Met Thr
            755                 760                 765
Phe Lys Ile Ile Ala Leu Asp Pro Tyr Tyr Tyr Phe Gln Gln Gly
            770                 775                 780
Trp Asn Ile Phe Asp Ser Ile Val Ile Leu Ser Leu Met Glu
            785                 790                 795
Leu Gly Leu Ser Arg Met Ser Asn Leu Ser Val Leu Arg Ser Phe
            800                 805                 810
```

-continued

```
Arg Leu Leu Arg Val Phe Lys Leu Ala Lys Ser Trp Pro Thr Leu
            815                 820                 825

Asn Thr Leu Ile Lys Ile Ile Gly Asn Ser Val Gly Ala Leu Gly
            830                 835                 840

Asn Leu Thr Leu Val Leu Ala Ile Ile Val Phe Ile Phe Ala Val
            845                 850                 855

Val Gly Met Gln Leu Phe Gly Lys Asn Tyr Ser Glu Leu Arg Asp
            860                 865                 870

Ser Asp Ser Gly Leu Leu Pro Arg Trp His Met Met Asp Phe Phe
            875                 880                 885

His Ala Phe Leu Ile Ile Phe Arg Ile Leu Cys Gly Glu Trp Ile
            890                 895                 900

Glu Thr Met Trp Asp Cys Met Glu Val Ser Gly Gln Ser Leu Cys
            905                 910                 915

Leu Leu Val Phe Leu Leu Val Met Val Ile Gly Asn Leu Val Val
            920                 925                 930

Leu Asn Leu Phe Leu Ala Leu Leu Ser Ser Phe Ser Ala Asp
            935                 940                 945

Asn Leu Thr Ala Pro Asp Glu Asp Arg Glu Met Asn Asn Leu Gln
            950                 955                 960

Leu Ala Leu Ala Arg Ile Gln Arg Gly Leu Arg Phe Val Lys Arg
            965                 970                 975

Thr Thr Trp Asp Phe Cys Cys Gly Leu Leu Arg His Arg Pro Gln
            980                 985                 990

Lys Pro Ala Ala Leu Ala Ala Gln Gly Gln Leu Pro Ser Cys Ile
            995                1000                1005

Ala Thr Pro Tyr Ser Pro Pro Pro Glu Thr Glu Lys Val Pro
           1010                1015                1020

Pro Thr Arg Lys Glu Thr Gln Phe Glu Glu Gly Glu Gln Pro Gly
           1025                1030                1035

Gln Gly Thr Pro Gly Asp Pro Glu Pro Val Cys Val Pro Ile Ala
           1040                1045                1050

Val Ala Glu Ser Asp Thr Asp Asp Gln Glu Glu Asp Glu Glu Asn
           1055                1060                1065

Ser Leu Gly Thr Glu Glu Glu Ser Ser Lys Gln Gln Glu Ser Gln
           1070                1075                1080

Pro Val Ser Gly Trp Pro Arg Gly Pro Pro Asp Ser Arg Thr Trp
           1085                1090                1095

Ser Gln Val Ser Ala Thr Ala Ser Ser Glu Ala Glu Ala Ser Ala
           1100                1105                1110

Ser Gln Ala Asp Trp Arg Gln Gln Trp Lys Ala Glu Pro Gln Ala
           1115                1120                1125

Pro Gly Cys Gly Glu Thr Pro Glu Asp Ser Cys Ser Glu Gly Ser
           1130                1135                1140

Thr Ala Asp Met Thr Asn Thr Ala Glu Leu Leu Glu Gln Ile Pro
           1145                1150                1155

Asp Leu Gly Gln Asp Val Lys Asp Pro Glu Asp Cys Phe Thr Glu
           1160                1165                1170

Gly Cys Val Arg Arg Cys Pro Cys Cys Ala Val Asp Thr Thr Gln
           1175                1180                1185

Ala Pro Gly Lys Val Trp Trp Arg Leu Arg Lys Thr Cys Tyr His
           1190                1195                1200

Ile Val Glu His Ser Trp Phe Glu Thr Phe Ile Ile Phe Met Ile
```

-continued

```
                1205                1210                1215
Leu Leu Ser Ser Gly Ala Leu Ala Phe Glu Asp Ile Tyr Leu Glu
                1220                1225                1230
Glu Arg Lys Thr Ile Lys Val Leu Leu Glu Tyr Ala Asp Lys Met
                1235                1240                1245
Phe Thr Tyr Val Phe Val Leu Glu Met Leu Leu Lys Trp Val Ala
                1250                1255                1260
Tyr Gly Phe Lys Lys Tyr Phe Thr Asn Ala Trp Cys Trp Leu Asp
                1265                1270                1275
Phe Leu Ile Val Asp Val Ser Leu Val Ser Leu Val Ala Asn Thr
                1280                1285                1290
Leu Gly Phe Ala Glu Met Gly Pro Ile Lys Ser Leu Arg Thr Leu
                1295                1300                1305
Arg Ala Leu Arg Pro Leu Arg Ala Leu Ser Arg Phe Glu Gly Met
                1310                1315                1320
Arg Val Val Val Asn Ala Leu Val Gly Ala Ile Pro Ser Ile Met
                1325                1330                1335
Asn Val Leu Leu Val Cys Leu Ile Phe Trp Leu Ile Phe Ser Ile
                1340                1345                1350
Met Gly Val Asn Leu Phe Ala Gly Lys Phe Gly Arg Cys Ile Asn
                1355                1360                1365
Gln Thr Glu Gly Asp Leu Pro Leu Asn Tyr Thr Ile Val Asn Asn
                1370                1375                1380
Lys Ser Gln Cys Glu Ser Leu Asn Leu Thr Gly Glu Leu Tyr Trp
                1385                1390                1395
Thr Lys Val Lys Val Asn Phe Asp Asn Val Gly Ala Gly Tyr Leu
                1400                1405                1410
Ala Leu Leu Gln Val Ala Thr Phe Lys Gly Trp Met Asp Ile Met
                1415                1420                1425
Tyr Ala Ala Val Asp Ser Arg Gly Tyr Glu Glu Gln Pro Gln Trp
                1430                1435                1440
Glu Tyr Asn Leu Tyr Met Tyr Ile Tyr Phe Val Ile Phe Ile Ile
                1445                1450                1455
Phe Gly Ser Phe Phe Thr Leu Asn Leu Phe Ile Gly Val Ile Ile
                1460                1465                1470
Asp Asn Phe Asn Gln Gln Lys Lys Lys Leu Gly Gly Gln Asp Ile
                1475                1480                1485
Phe Met Thr Glu Glu Gln Lys Lys Tyr Tyr Asn Ala Met Lys Lys
                1490                1495                1500
Leu Gly Ser Lys Lys Pro Gln Lys Pro Ile Pro Arg Pro Leu Asn
                1505                1510                1515
Lys Tyr Gln Gly Phe Ile Phe Asp Ile Val Thr Lys Gln Ala Phe
                1520                1525                1530
Asp Val Thr Ile Met Phe Leu Ile Cys Leu Asn Met Val Thr Met
                1535                1540                1545
Met Val Glu Thr Asp Asp Gln Ser Pro Glu Lys Ile Asn Ile Leu
                1550                1555                1560
Ala Lys Ile Asn Leu Leu Phe Val Ala Ile Phe Thr Gly Glu Cys
                1565                1570                1575
Ile Val Lys Leu Ala Ala Leu Arg His Tyr Tyr Phe Thr Asn Ser
                1580                1585                1590
Trp Asn Ile Phe Asp Phe Val Val Val Ile Leu Ser Ile Val Gly
                1595                1600                1605
```

```
Thr Val Leu Ser Asp Ile Ile Gln Lys Tyr Phe Phe Ser Pro Thr
            1610                1615                1620
Leu Phe Arg Val Ile Arg Leu Ala Arg Ile Gly Arg Ile Leu Arg
            1625                1630                1635
Leu Ile Arg Gly Ala Lys Gly Ile Arg Thr Leu Leu Phe Ala Leu
            1640                1645                1650
Met Met Ser Leu Pro Ala Leu Phe Asn Ile Gly Leu Leu Leu Phe
            1655                1660                1665
Leu Val Met Phe Ile Tyr Ser Ile Phe Gly Met Ala Asn Phe Ala
            1670                1675                1680
Tyr Val Lys Trp Glu Ala Gly Ile Asp Asp Met Phe Asn Phe Gln
            1685                1690                1695
Thr Phe Ala Asn Ser Met Leu Cys Leu Phe Gln Ile Thr Thr Ser
            1700                1705                1710
Ala Gly Trp Asp Gly Leu Leu Ser Pro Ile Leu Asn Thr Gly Pro
            1715                1720                1725
Pro Tyr Cys Asp Pro Thr Leu Pro Asn Ser Asn Gly Ser Arg Gly
            1730                1735                1740
Asp Cys Gly Ser Pro Ala Val Gly Ile Leu Phe Phe Thr Thr Tyr
            1745                1750                1755
Ile Ile Ile Ser Phe Leu Ile Val Val Asn Met Tyr Ile Ala Ile
            1760                1765                1770
Ile Leu Glu Asn Phe Ser Val Ala Thr Glu Glu Ser Thr Glu Pro
            1775                1780                1785
Leu Ser Glu Asp Asp Phe Asp Met Phe Tyr Glu Ile Trp Glu Lys
            1790                1795                1800
Phe Asp Pro Glu Ala Thr Gln Phe Ile Glu Tyr Ser Val Leu Ser
            1805                1810                1815
Asp Phe Ala Asp Ala Leu Ser Glu Pro Leu Ile Arg Ala Lys Pro
            1820                1825                1830
Asn Gln Ile Ser Leu Ile Asn Met Asp Leu Pro Met Val Ser Gly
            1835                1840                1845
Asp Arg Ile His Cys Met Asp Ile Leu Phe Ala Phe Thr Lys Arg
            1850                1855                1860
Val Leu Gly Glu Ser Gly Glu Met Asp Ala Leu Lys Ile Gln Met
            1865                1870                1875
Glu Glu Lys Phe Met Ala Ala Asn Pro Ser Lys Ile Ser Tyr Glu
            1880                1885                1890
Pro Ile Thr Thr Thr Leu Arg Arg Lys His Glu Glu Val Ser Ala
            1895                1900                1905
Met Val Ile Gln Arg Ala Phe Arg Arg His Leu Leu Gln Arg Ser
            1910                1915                1920
Leu Lys His Ala Ser Phe Leu Phe Arg Gln Gln Ala Gly Ser Gly
            1925                1930                1935
Leu Ser Glu Glu Asp Ala Pro Glu Arg Glu Gly Leu Ile Ala Tyr
            1940                1945                1950
Val Met Ser Glu Asn Phe Ser Arg Pro Leu Gly Pro Pro Ser Ser
            1955                1960                1965
Ser Ser Ile Ser Ser Thr Ser Phe Pro Pro Ser Tyr Asp Ser Val
            1970                1975                1980
Thr Arg Ala Thr Ser Asp Asn Leu Gln Val Arg Gly Ser Asp Tyr
            1985                1990                1995
```

Ser His Ser Glu Asp Leu Ala Asp Phe Pro Pro Ser Pro Asp Arg
            2000                2005                2010

Asp Arg Glu Ser Ile Val
            2015

(2) INFORMATION FOR SEQ ID NO: 3:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO: 3:

ATGGCAAACT TCCTATTACC TCGG                                              24

(2) INFORMATION FOR SEQ ID NO: 4:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO: 4:

CACGATGGAC TCACGGTCCC TGTC                                              24

(2) INFORMATION FOR SEQ ID NO: 5:

(i) SEQUENCE CHARACTERISTICS:
        (A) LENGTH: 3069 bases
        (B) TYPE: nucleic acid
        (C) STRANDEDNESS: double
        (D) TOPOLOGY: linear (xi) SEQUENCE DESCRIPTION: SEQ ID NO: 5:

ATG GGG AAG GGG GTT GGA CGT GAT AAG TAT GAG CCT GCA GCT GTT            45
Met Gly Lys Gly Val Gly Arg Asp Lys Tyr Glu Pro Ala Ala Val
1               5                   10                  15

TCA GAA CAA GGT GAT AAA AAG GGC AAA AAG GGC AAA AAA GAC AGG            90
Ser Glu Gln Gly Asp Lys Lys Gly Lys Lys Gly Lys Lys Asp Arg
                20                  25                  30

GAC ATG GAT GAA CTG AAG AAA GAA GTT TCT ATG GAT GAT CAT AAA           135
Asp Met Asp Glu Leu Lys Lys Glu Val Ser Met Asp Asp His Lys
                35                  40                  45

CTT AGC CTT GAT GAA CTT CAT CGT AAA TAT GGA ACA GAC TTG AGC           180
Leu Ser Leu Asp Glu Leu His Arg Lys Tyr Gly Thr Asp Leu Ser
                50                  55                  60

CGG GGA TTA ACA TCT GCT CGT GCA GCT GAG ATC CTG GCG CGA GAT           225
Arg Gly Leu Thr Ser Ala Arg Ala Ala Glu Ile Leu Ala Arg Asp
                65                  70                  75

GGT CCC AAC GCC CTC ACT CCC CCT CCC ACT ACT CCT GAA TGG ATC           270
Gly Pro Asn Ala Leu Thr Pro Pro Pro Thr Thr Pro Glu Trp Ile
                80                  85                  90

AAG TTT TGT CGG CAG CTC TTT GGG GGG TTC TCA ATG TTA CTG TGG           315
Lys Phe Cys Arg Gln Leu Phe Gly Gly Phe Ser Met Leu Leu Trp
                95                  100                 105

ATT GGA GCG ATT CTT TGT TTC TTG GCT TAT AGC ATC CAA GCT GCT           360
Ile Gly Ala Ile Leu Cys Phe Leu Ala Tyr Ser Ile Gln Ala Ala
                110                 115                 120

ACA GAA GAG GAA CCT CAA AAC GAT AAT CTG TAC CTG GGT GTG GTG           405
Thr Glu Glu Glu Pro Gln Asn Asp Asn Leu Tyr Leu Gly Val Val
                125                 130                 135

```
                                                    -continued

CTA TCA GCC GTT GTA ATC ATA ACT GGT TGC TTC TCC TAC TAT CAA        450
Leu Ser Ala Val Val Ile Ile Thr Gly Cys Phe Ser Tyr Tyr Gln
            140                 145                 150

GAA GCT AAA AGT TCA AAG ATC ATG GAA TCC TTC AAA AAC ATG GTC        495
Glu Ala Lys Ser Ser Lys Ile Met Glu Ser Phe Lys Asn Met Val
            155                 160                 165

CCT CAG CAA GCC CTT GTG ATT CGA AAT GGT GAG AAA ATG AGC ATA        540
Pro Gln Gln Ala Leu Val Ile Arg Asn Gly Glu Lys Met Ser Ile
            170                 175                 180

AAT GCG GAG GAA GTT GTG GTT GGG GAT CTG GTG GAA GTA AAA GGA        585
Asn Ala Glu Glu Val Val Val Gly Asp Leu Val Glu Val Lys Gly
            185                 190                 195

GGA GAC CGA ATT CCT GCT GAC CTC AGA ATC ATA TCT GCA AAT GGC        630
Gly Asp Arg Ile Pro Ala Asp Leu Arg Ile Ile Ser Ala Asn Gly
            200                 205                 210

TGC AAG GTG GAT AAC TCC TCG CTC ACT GGT GAA TCA GAA CCC CAG        675
Cys Lys Val Asp Asn Ser Ser Leu Thr Gly Glu Ser Glu Pro Gln
            215                 220                 225

ACT AGG TCT CCA GAT TTC ACA AAT GAA AAC CCC CTG GAG ACG AGG        720
Thr Arg Ser Pro Asp Phe Thr Asn Glu Asn Pro Leu Glu Thr Arg
            230                 235                 240

AAC ATT GCC TTC TTT TCA ACA AAT TGT GTT GAA GGC ACC GCA CGT        765
Asn Ile Ala Phe Phe Ser Thr Asn Cys Val Glu Gly Thr Ala Arg
            245                 250                 255

GGT ATT GTT GTC TAC ACT GGG GAT CGC ACT GTG ATG GGA AGA ATT        810
Gly Ile Val Val Tyr Thr Gly Asp Arg Thr Val Met Gly Arg Ile
            260                 265                 270

GCC ACA CTT GCT TCT GGG CTG GAA GGA GGC CAG ACC CCC ATT GCT        855
Ala Thr Leu Ala Ser Gly Leu Glu Gly Gly Gln Thr Pro Ile Ala
            275                 280                 285

GCA GAA ATT GAA CAT TTT ATC CAC ATC ATC ACG GGT GTG GCT GTG        900
Ala Glu Ile Glu His Phe Ile His Ile Ile Thr Gly Val Ala Val
            290                 295                 300

TTC CTG GGT GTG TCT TTC TTC ATC CTT TCT CTC ATC CTT GAG TAC        945
Phe Leu Gly Val Ser Phe Phe Ile Leu Ser Leu Ile Leu Glu Tyr
            305                 310                 315

ACC TGG CTT GAG GCT GTC ATC TTC CTC ATC GGT ATC ATC GTA GCC        990
Thr Trp Leu Glu Ala Val Ile Phe Leu Ile Gly Ile Ile Val Ala
            320                 325                 330

AAT GTG CCG GAA GGT TTG CTG GCC ACT GTC ACG GTC TGT CTG ACA       1035
Asn Val Pro Glu Gly Leu Leu Ala Thr Val Thr Val Cys Leu Thr
            335                 340                 345

CTT ACT GCC AAA CGC ATG GCA AGG AAA AAC TGC TTA GTG AAG AAC       1080
Leu Thr Ala Lys Arg Met Ala Arg Lys Asn Cys Leu Val Lys Asn
            350                 355                 360

TTA GAA GCT GTG GAG ACC TTG GGG TCC ACG TCC ACC ATC TGC TCT       1125
Leu Glu Ala Val Glu Thr Leu Gly Ser Thr Ser Thr Ile Cys Ser
            365                 370                 375

GAT AAA ACT GGA ACT CTG ACT CAG AAC CGG ATG ACA GTG GCC CAC       1170
Asp Lys Thr Gly Thr Leu Thr Gln Asn Arg Met Thr Val Ala His
            380                 385                 390

ATG TGG TTT GAC AAT CAA ATC CAT GAA GCT GAT ACG ACA GAG AAT       1215
Met Trp Phe Asp Asn Gln Ile His Glu Ala Asp Thr Thr Glu Asn
            395                 400                 405

CAG AGT GGT GTC TCT TTT GAC AAG ACT TCA GCT ACC TGG CTT GCT       1260
Gln Ser Gly Val Ser Phe Asp Lys Thr Ser Ala Thr Trp Leu Ala
            410                 415                 420

CTG TCC AGA ATT GCA GGT CTT TGT AAC AGG GCA GTG TTT CAG GCT       1305
Leu Ser Arg Ile Ala Gly Leu Cys Asn Arg Ala Val Phe Gln Ala
            425                 430                 435
```

```
AAC CAG GAA AAC CTA CCT ATT CTT AAG CGG GCA GTT GCA GGA GAT         1350
Asn Gln Glu Asn Leu Pro Ile Leu Lys Arg Ala Val Ala Gly Asp
                440                 445                 450

GCC TCT GAG TCA GCA CTC TTA AAG TGC ATA GAG CTG TGC TGT GGT         1395
Ala Ser Glu Ser Ala Leu Leu Lys Cys Ile Glu Leu Cys Cys Gly
                455                 460                 465

TTC GTG AAG GAG ATG AGA GAA AGA TAC GCC AAA ATC GTC GAG ATA         1440
Ser Val Lys Glu Met Arg Glu Arg Tyr Ala Lys Ile Val Glu Ile
                470                 475                 480

CCC TTC AAC TCC ACC AAC AAG TAC CAG TTG TCT ATT CAT AAG AAC         1485
Pro Phe Asn Ser Thr Asn Lys Tyr Gln Leu Ser Ile His Lys Asn
                485                 490                 495

CCC AAC ACA TCG GAG CCC CAA CAC CTG TTG GTG ATG AAG GGC GCC         1530
Pro Asn Thr Ser Glu Pro Gln His Leu Leu Val Met Lys Gly Ala
                500                 505                 510

CCA GAA AGG ATC CTA GAC CGT TGC AGC TCT ATC CTC CTC CAC GGC         1575
Pro Glu Arg Ile Leu Asp Arg Cys Ser Ser Ile Leu Leu His Gly
                515                 520                 525

AAG GAG CAG CCC CTG GAT GAG GAG CTG AAA GAC GCC TTT CAG AAC         1620
Lys Glu Gln Pro Leu Asp Glu Glu Leu Lys Asp Ala Phe Gln Asn
                530                 535                 540

GCC TAT TTG GAG CTG GGG GGC CTC GGA GAA CGA GTC CTA GGT TTC         1665
Ala Tyr Leu Glu Leu Gly Gly Leu Gly Glu Arg Val Leu Gly Phe
                545                 550                 555

TGC CAC CTC TTT CTG CCA GAT GAA CAG TTT CCT GAA GGG TTC CAG         1710
Cys His Leu Phe Leu Pro Asp Glu Gln Phe Pro Glu Gly Phe Gln
                560                 565                 570

TTT GAC ACT GAC GAT GTG AAT TTC CCT ATC GAT AAT CTG TGC TTC         1755
Phe Asp Thr Asp Asp Val Asn Phe Pro Ile Asp Asn Leu Cys Phe
                575                 580                 585

GTT GGG CTC ATC TCC ATG ATT GAC CCT CCA CGG GCG GCC GTT CCT         1800
Val Gly Leu Ile Ser Met Ile Asp Pro Pro Arg Ala Ala Val Pro
                590                 595                 600

GAT GCC GTG GGC AAA TGT CGA AGT GCT GGA ATT AAG GTC ATC ATG         1845
Asp Ala Val Gly Lys Cys Arg Ser Ala Gly Ile Lys Val Ile Met
                605                 610                 615

GTC ACA GGA GAC CAT CCA ATC ACA GCT AAA GCT ATT GCC AAA GGT         1890
Val Thr Gly Asp His Pro Ile Thr Ala Lys Ala Ile Ala Lys Gly
                620                 625                 630

GTG GGC ATC ATC TCA GAA GGC ATG GAG ACC GTG GAA GAC ATT GCT         1935
Val Gly Ile Ile Ser Glu Gly Met Glu Thr Val Glu Asp Ile Ala
                635                 640                 645

GCC CGC CTC AAC ATC CCA GTC AGC CAG GTG AAC CCC AGG GAT GCC         1980
Ala Arg Leu Asn Ile Pro Val Ser Gln Val Asn Pro Arg Asp Ala
                650                 655                 660

AAG GCC TGC GTA GTA CAC GGC AGT GAT CTA AAG GAC ATG ACC TCC         2025
Lys Ala Cys Val Val His Gly Ser Asp Leu Lys Asp Met Thr Ser
                665                 670                 675

GAG CAG CTG GAT GAC ATT TTG AAG TAC CAC ACT GAG ATA GTG TTT         2070
Glu Gln Leu Asp Asp Ile Leu Lys Tyr His Thr Glu Ile Val Phe
                680                 685                 690

GCC AGG ACC TCC CCT CAG CAG AAG CTC ATC ATT GTG GAA GGC TGC         2115
Ala Arg Thr Ser Pro Gln Gln Lys Leu Ile Ile Val Glu Gly Cys
                695                 700                 705

CAA AGA CAG GGT GCT ATC GTG GCT GTG ACT GGT GAC GGT GTG AAT         2160
Gln Arg Gln Gly Ala Ile Val Ala Val Thr Gly Asp Gly Val Asn
                710                 715                 720

GAC TCT CCA GCT TTG AAG AAA GCA GAC ATT GGG GTT GCT ATG GGG         2205
Asp Ser Pro Ala Leu Lys Lys Ala Asp Ile Gly Val Ala Met Gly
```

```
                            725                 730                 735
ATT GCT GGC TCA GAT GTG TCC AAG CAA GCT GCT GAC ATG ATT CTT         2250
Ile Ala Gly Ser Asp Val Ser Lys Gln Ala Ala Asp Met Ile Leu
                740                 745                 750

CTG GAT GAC AAC TTT GCC TCA ATT GTG ACT GGA GTA GAG GAA GGT         2295
Leu Asp Asp Asn Phe Ala Ser Ile Val Thr Gly Val Glu Glu Gly
                755                 760                 765

CGT CTG ATC TTT GAT AAC TTG AAG AAA TCC ATT GCT TAT ACC TTA         2340
Arg Leu Ile Phe Asp Asn Leu Lys Lys Ser Ile Ala Tyr Thr Leu
                770                 775                 780

ACC AGT AAC ATT CCC GAG ATC ACC CCG TTC CTG ATA TTT ATT ATT         2385
Thr Ser Asn Ile Pro Glu Ile Thr Pro Phe Leu Ile Phe Ile Ile
                785                 790                 795

GCA AAC ATT CCA CTA CCA CTG GGG ACT GTC ACC ATC CTC TGC ATT         2430
Ala Asn Ile Pro Leu Pro Leu Gly Thr Val Thr Ile Leu Cys Ile
                800                 805                 810

GAC TTG GGC ACT GAC ATG GTT CCT GCC ATC TCC CTG GCT TAT GAG         2475
Asp Leu Gly Thr Asp Met Val Pro Ala Ile Ser Leu Ala Tyr Glu
                815                 820                 825

CAG GCT GAG AGT GAC ATC ATG AAG AGA CAG CCC AGA AAT CCC AAA         2520
Gln Ala Glu Ser Asp Ile Met Lys Arg Gln Pro Arg Asn Pro Lys
                830                 835                 840

ACA GAC AAA CTT GTG AAT GAG CGG CTG ATC AGC ATG GCC TAT GGG         2565
Thr Asp Lys Leu Val Asn Glu Arg Leu Ile Ser Met Ala Tyr Gly
                845                 850                 855

CAG ATT GGA ATG ATC CAG GCC CTG GGA GGC TTC TTT ACT TAC TTT         2610
Gln Ile Gly Met Ile Gln Ala Leu Gly Gly Phe Phe Thr Tyr Phe
                860                 865                 870

GTG ATT CTG GCT GAG AAC GGC TTC CTC CCA ATT CAC CTG TTG GGC         2655
Val Ile Leu Ala Glu Asn Gly Phe Leu Pro Ile His Leu Leu Gly
                875                 880                 885

CTC CGA GTG GAC TGG GAT GAC CGC TGG ATC AAC GAT GTG GAA GAC         2700
Leu Arg Val Asp Trp Asp Asp Arg Trp Ile Asn Asp Val Glu Asp
                890                 895                 900

AGC TAC GGG CAG CAG TGG ACC TAT GAG CAG AGG AAA ATC GTG GAG         2745
Ser Tyr Gly Gln Gln Trp Thr Tyr Glu Gln Arg Lys Ile Val Glu
                905                 910                 915

TTC ACC TGC CAC ACA GCC TTC TTC GTC AGT ATC GTG GTG GTG CAG         2790
Phe Thr Cys His Thr Ala Phe Phe Val Ser Ile Val Val Val Gln
                920                 925                 930

TGG GCC GAC TTG GTC ATC TGT AAG ACC AGG AGG AAT TCG GTC TTC         2835
Trp Ala Asp Leu Val Ile Cys Lys Thr Arg Arg Asn Ser Val Phe
                935                 940                 945

CAG CAG GGG ATG AAG AAC AAG ATC TTG ATA TTT GGC CTC TTT GAA         2880
Gln Gln Gly Met Lys Asn Lys Ile Leu Ile Phe Gly Leu Phe Glu
                950                 955                 960

GAG ACA GCC CTG GCT GCT TTC CTT TCC TAC TGC CCT GGA ATG GGT         2925
Glu Thr Ala Leu Ala Ala Phe Leu Ser Tyr Cys Pro Gly Met Gly
                965                 970                 975

GTT GCT CTT AGG ATG TAT CCC CTC AAA CCT ACC TGG TGG TTC TGT         2970
Val Ala Leu Arg Met Tyr Pro Leu Lys Pro Thr Trp Trp Phe Cys
                980                 985                 990

GCC TTC CCC TAC TCT CTT CTC ATC TTC GTA TAT GAC GAA GTC AGA         3015
Ala Phe Pro Tyr Ser Leu Leu Ile Phe Val Tyr Asp Glu Val Arg
                995                 1000                1005

AAA CTC ATC ATC AGG CGA CGC CCT GGC GGC TGG GTG GAG AAG GAA         3060
Lys Leu Ile Ile Arg Arg Arg Pro Gly Gly Trp Val Glu Lys Glu
                1010                1015                1020

ACC TAC TAT                                                         3069
```

Thr Tyr Tyr (2) INFORMATION FOR SEQ ID NO: 6:

(i) SEQUENCE CHARACTERISTICS:
        (A) LENGTH: 1023 amino acids
        (B) TYPE: amino acid
        (C) STRANDEDNESS: single
        (D) TOPOLOGY: unknown (xi) SEQUENCE DESCRIPTION: SEQ ID NO: 6:

```
Met Gly Lys Gly Val Gly Arg Asp Lys Tyr Glu Pro Ala Ala Val
 1               5                  10                  15

Ser Glu Gln Glu Asp Lys Lys Glu Lys Glu Lys Lys Asp Arg
                20                  25                  30

Asp Met Asp Glu Leu Lys Lys Glu Val Ser Met Asp Asp His Lys
                35                  40                  45

Leu Ser Leu Asp Glu Leu His Arg Lys Tyr Gly Thr Asp Leu Ser
                50                  55                  60

Arg Gly Leu Thr Ser Ala Arg Ala Ala Glu Ile Leu Ala Arg Asp
                65                  70                  75

Gly Pro Asn Ala Leu Thr Pro Pro Thr Thr Pro Glu Trp Ile
                80                  85                  90

Lys Phe Cys Arg Gln Leu Phe Gly Gly Phe Ser Met Leu Leu Trp
                95                 100                 105

Ile Gly Ala Ile Leu Cys Phe Leu Ala Tyr Ser Ile Gln Ala Ala
               110                 115                 120

Thr Glu Glu Glu Pro Gln Asn Asp Asn Leu Tyr Leu Gly Val Val
               125                 130                 135

Leu Ser Ala Val Val Ile Ile Thr Gly Cys Phe Ser Tyr Tyr Gln
               140                 145                 150

Glu Ala Lys Ser Ser Lys Ile Met Glu Ser Phe Lys Asn Met Val
               155                 160                 165

Pro Gln Gln Ala Leu Val Ile Arg Asn Gly Glu Lys Met Ser Ile
               170                 175                 180

Asn Ala Glu Glu Val Val Val Gly Asp Leu Val Glu Val Lys Gly
               185                 190                 195

Gly Asp Arg Ile Pro Ala Asp Leu Arg Ile Ile Ser Ala Asn Gly
               200                 205                 210

Cys Lys Val Asp Asn Ser Ser Leu Thr Gly Glu Ser Glu Pro Gln
               215                 220                 225

Thr Arg Ser Pro Asp Phe Thr Asn Glu Asn Pro Leu Glu Thr Arg
               230                 235                 240

Asn Ile Ala Phe Phe Ser Thr Asn Cys Val Glu Gly Thr Ala Arg
               245                 250                 255

Gly Ile Val Val Tyr Thr Gly Asp Arg Thr Val Met Gly Arg Ile
               260                 265                 270

Ala Thr Leu Ala Ser Gly Leu Glu Gly Gly Gln Thr Pro Ile Ala
               275                 280                 285

Ala Glu Ile Glu His Phe Ile His Ile Ile Thr Gly Val Ala Val
               290                 295                 300

Phe Leu Gly Val Ser Phe Phe Ile Leu Ser Leu Ile Leu Glu Tyr
               305                 310                 315

Thr Trp Leu Glu Ala Val Ile Phe Leu Ile Gly Ile Ile Val Ala
               320                 325                 330
```

-continued

```
Asn Val Pro Glu Gly Leu Leu Ala Thr Val Thr Val Cys Leu Thr
                335                 340                 345

Leu Thr Ala Lys Arg Met Ala Arg Lys Asn Cys Leu Val Lys Asn
            350                 355                 360

Leu Glu Ala Val Glu Thr Leu Gly Ser Thr Ser Thr Ile Cys Ser
        365                 370                 375

Asp Lys Thr Gly Thr Leu Thr Gln Asn Arg Met Thr Val Ala His
    380                 385                 390

Met Trp Phe Asp Asn Gln Ile His Glu Ala Asp Thr Thr Glu Asn
395                 400                 405

Gln Ser Gly Val Ser Phe Asp Lys Thr Ser Ala Thr Trp Leu Ala
            410                 415                 420

Leu Ser Arg Ile Ala Gly Leu Cys Asn Arg Ala Val Phe Gln Ala
        425                 430                 435

Asn Gln Glu Asn Leu Pro Ile Leu Lys Arg Ala Val Ala Gly Asp
    440                 445                 450

Ala Ser Glu Ser Ala Leu Leu Lys Cys Ile Glu Leu Cys Cys Gly
455                 460                 465

Ser Val Lys Glu Met Arg Glu Arg Tyr Ala Lys Ile Val Glu Ile
            470                 475                 480

Pro Phe Asn Ser Thr Asn Lys Tyr Gln Leu Ser Ile His Lys Asn
        485                 490                 495

Pro Asn Thr Ser Glu Pro Gln His Leu Leu Val Met Lys Gly Ala
    500                 505                 510

Pro Glu Arg Ile Leu Asp Arg Cys Ser Ser Ile Leu Leu His Gly
515                 520                 525

Lys Glu Gln Pro Leu Asp Glu Leu Lys Asp Ala Phe Gln Asn
            530                 535                 540

Ala Tyr Leu Glu Leu Gly Gly Leu Gly Glu Arg Val Leu Gly Phe
        545                 550                 555

Cys His Leu Phe Leu Pro Asp Glu Gln Phe Pro Glu Gly Phe Gln
    560                 565                 570

Phe Asp Thr Asp Asp Val Asn Phe Pro Ile Asp Asn Leu Cys Phe
575                 580                 585

Val Gly Leu Ile Ser Met Ile Asp Pro Pro Arg Ala Ala Val Pro
            590                 595                 600

Asp Ala Val Gly Lys Cys Arg Ser Ala Gly Ile Lys Val Ile Met
        605                 610                 615

Val Thr Gly Asp His Pro Ile Thr Ala Lys Ala Ile Ala Lys Gly
    620                 625                 630

Val Gly Ile Ile Ser Glu Gly Asn Glu Thr Val Glu Asp Ile Ala
635                 640                 645

Ala Arg Leu Asn Ile Pro Val Ser Gln Val Asn Pro Arg Asp Ala
            650                 655                 660

Lys Ala Cys Val Val His Gly Ser Asp Leu Lys Asp Met Thr Ser
        665                 670                 675

Glu Gln Leu Asp Asp Ile Leu Lys Tyr His Thr Glu Ile Val Phe
    680                 685                 690

Ala Arg Thr Ser Pro Gln Gln Lys Leu Ile Ile Val Glu Gly Cys
695                 700                 705

Gln Arg Gln Gly Ala Ile Val Ala Val Thr Gly Asp Gly Val Asn
            710                 715                 720

Asp Ser Pro Ala Leu Lys Lys Ala Asp Ile Gly Val Ala Met Gly
```

```
                    725                 730                 735
Ile Ala Gly Ser Asp Val Ser Lys Gln Ala Ala Asp Met Ile Leu
                740                 745                 750
Leu Asp Asp Asn Phe Ala Ser Ile Val Thr Gly Val Glu Glu Gly
                755                 760                 765
Arg Leu Ile Phe Asp Asn Leu Lys Lys Ser Ile Ala Tyr Thr Leu
                770                 775                 780
Thr Ser Asn Ile Pro Glu Ile Thr Pro Phe Leu Ile Phe Ile Ile
                785                 790                 795
Ala Asn Ile Pro Leu Pro Leu Gly Thr Val Thr Ile Leu Cys Ile
                800                 805                 810
Asp Leu Gly Thr Asp Met Val Pro Ala Ile Ser Leu Ala Tyr Glu
                815                 820                 825
Gln Ala Glu Ser Asp Ile Met Lys Arg Gln Pro Arg Asn Pro Lys
                830                 835                 840
Thr Asp Lys Leu Val Asn Glu Arg Leu Ile Ser Met Ala Tyr Gly
                845                 850                 855
Gln Ile Gly Met Ile Gln Ala Leu Gly Gly Phe Phe Thr Tyr Phe
                860                 865                 870
Val Ile Leu Ala Glu Asn Gly Phe Leu Pro Ile His Leu Leu Gly
                875                 880                 885
Leu Arg Val Asp Trp Asp Asp Arg Trp Ile Asn Asp Val Glu Asp
                890                 895                 900
Ser Tyr Gly Gln Gln Trp Thr Tyr Glu Gln Arg Lys Ile Val Glu
                905                 910                 915
Phe Thr Cys His Thr Ala Phe Phe Val Ser Ile Val Val Val Gln
                920                 925                 930
Trp Ala Asp Leu Val Ile Cys Lys Thr Arg Arg Asn Ser Val Phe
                935                 940                 945
Gln Gln Gly Met Lys Asn Lys Ile Leu Ile Phe Gly Leu Phe Glu
                950                 955                 960
Glu Thr Ala Leu Ala Ala Phe Leu Ser Tyr Cys Pro Gly Met Gly
                965                 970                 975
Val Ala Leu Arg Met Tyr Pro Leu Lys Pro Thr Trp Trp Phe Cys
                980                 985                 990
Ala Phe Pro Tyr Ser Leu Leu Ile Phe Val Tyr Asp Glu Val Arg
                995                 1000                1005
Lys Leu Ile Ile Arg Arg Arg Pro Gly Gly Trp Val Glu Lys Glu
                1010                1015                1020
Thr Tyr Tyr (2) INFORMATION FOR SEQ ID NO: 7:

(i) SEQUENCE CHARACTERISTICS:
        (A) LENGTH: 909 bases
        (B) TYPE: nucleic acid
        (C) STRANDEDNESS: double
        (D) TOPOLOGY: linear (xi) SEQUENCE DESCRIPTION: SEQ ID NO: 7:

ATG GCC CGC GGG AAA GCC AAG GAG GAG GGC AGC TGG AAG AAA TTC        45
Met Ala Arg Gly Lys Ala Lys Glu Glu Gly Ser Trp Lys Lys Phe
 1               5                  10                  15

ATC TGG AAC TCA GAG AAG AAG GAG TTT CTG GGC AGG ACC GGT GGC        90
Ile Trp Asn Ser Glu Lys Lys Glu Phe Leu Gly Arg Thr Gly Gly
                20                  25                  30
```

-continued

```
AGT TGG TTT AAG ATC CTT CTA TTC TAC GTA ATA TTT TAT GGC TGC        135
Ser Trp Phe Lys Ile Leu Leu Phe Tyr Val Ile Phe Tyr Gly Cys
             35                  40                  45

CTG GCT GGC ATC TTC ATC GGA ACC ATC CAA GTG ATG CTG CTC ACC        180
Leu Ala Gly Ile Phe Ile Gly Thr Ile Gln Val Met Leu Leu Thr
             50                  55                  60

ATC AGT GAA TTT AAG CCC ACA TAT CAG GAC CGA GTG GCC CCG CCA        225
Ile Ser Glu Phe Lys Pro Thr Tyr Gln Asp Arg Val Ala Pro Pro
             65                  70                  75

GGA TTA ACA CAG ATT CCT CAG ATC CAG AAG ACT GAA ATT TCC TTT        270
Gly Leu Thr Gln Ile Pro Gln Ile Gln Lys Thr Glu Ile Ser Phe
             80                  85                  90

CGT CCT AAT GAT CCC AAG AGC TAT GAG GCA TAT GTA CTG AAC ATA        315
Arg Pro Asn Asp Pro Lys Ser Tyr Glu Ala Tyr Val Leu Asn Ile
             95                 100                 105

GTT AGG TTC CTG GAA AAG TAC AAA GAT TCA GCC CAG AGG GAT GAC        360
Val Arg Phe Leu Glu Lys Tyr Lys Asp Ser Ala Gln Arg Asp Asp
            110                 115                 120

ATG ATT TTT GAA GAT TGT GGC GAT GTG CCC AGT GAA CCG AAA GAA        405
Met Ile Phe Glu Asp Cys Gly Asp Val Pro Ser Glu Pro Lys Glu
            125                 130                 135

CGA GGA GAC TTT AAT CAT GAA CGA GGA GAG CGA AAG GTC TGC AGA        450
Arg Gly Asp Phe Asn His Glu Arg Gly Glu Arg Lys Val Cys Arg
            140                 145                 150

TTC AAG CTT GAA TGG CTG GGA AAT TGC TCT GGA TTA AAT GAT GAA        495
Phe Lys Leu Glu Trp Leu Gly Asn Cys Ser Gly Leu Asn Asp Glu
            155                 160                 165

ACT TAT GGC TAC AAA GAG GGC AAA CCG TGC ATT ATT ATA AAG CTC        540
Thr Tyr Gly Tyr Lys Glu Gly Lys Pro Cys Ile Ile Ile Lys Leu
            170                 175                 180

AAC CGA GTT CTA GGC TTC AAA CCT AAG CCT CCC AAG AAT GAG TCC        585
Asn Arg Val Leu Gly Phe Lys Pro Lys Pro Pro Lys Asn Glu Ser
            185                 190                 195

TTG GAG ACT TAC CCA GTG ATG AAG TAT AAC CCA AAT GTC CTT CCC        630
Leu Glu Thr Tyr Pro Val Met Lys Tyr Asn Pro Asn Val Leu Pro
            200                 205                 210

GTT CAG TGC ACT GGC AAG CGA GAT GAA GAT AAG GAT AAA GTT GGA        675
Val Gln Cys Thr Gly Lys Arg Asp Glu Asp Lys Asp Lys Val Gly
            215                 220                 225

AAT GTG GAG TAT TTT GGA CTG GGC AAC TCC CCT GGT TTT CCT CTG        720
Asn Val Glu Tyr Phe Gly Leu Gly Asn Ser Pro Gly Phe Pro Leu
            230                 235                 240

CAG TAT TAT CCG TAC TAT GGC AAA CTC CTG CAG CCC AAA TAC CTG        765
Gln Tyr Tyr Pro Tyr Tyr Gly Lys Leu Leu Gln Pro Lys Tyr Leu
            245                 250                 255

CAG CCC CTG CTG GCC GTA CAG TTC ACC AAT CTT ACC ATG GAC ACT        810
Gln Pro Leu Leu Ala Val Gln Phe Thr Asn Leu Thr Met Asp Thr
            260                 265                 270

GAA ATT CGC ATA GAG TGT AAG GCG TAC GGT GAG AAC ATT GGG TAC        855
Glu Ile Arg Ile Glu Cys Lys Ala Tyr Gly Glu Asn Ile Gly Tyr
            275                 280                 285

AGT GAG AAA GAC CGT TTT CAG GGA CGT TTT GAT GTA AAA ATT GAA        900
Ser Glu Lys Asp Arg Phe Gln Gly Arg Phe Asp Val Lys Ile Glu
            290                 295                 300

GTT AAG AGC                                                        909
Val Lys Ser
```

(2) INFORMATION FOR SEQ ID NO: 8:

(i) SEQUENCE CHARACTERISTICS:
    (A) LENGTH: 303 amino acids
    (B) TYPE: amino acid
    (C) STRANDEDNESS: single
    (D) TOPOLOGY: unknown (xi) SEQUENCE DESCRIPTION: SEQ ID NO: 8:

Met Ala Arg Gly Lys Ala Lys Glu Glu Gly Ser Trp Lys Lys Phe
1               5                   10                  15

Ile Trp Asn Ser Glu Lys Lys Glu Phe Leu Gly Arg Thr Gly Gly
                20                  25                  30

Ser Trp Phe Lys Ile Leu Leu Phe Tyr Val Ile Phe Tyr Gly Cys
                35                  40                  45

Leu Ala Gly Ile Phe Ile Gly Thr Ile Gln Val Met Leu Leu Thr
                50                  55                  60

Ile Ser Glu Phe Lys Pro Thr Tyr Gln Asp Arg Val Ala Pro Pro
                65                  70                  75

Gly Leu Thr Gln Ile Pro Gln Ile Gln Lys Thr Glu Ile Ser Phe
                80                  85                  90

Arg Pro Asn Asp Pro Lys Ser Tyr Glu Ala Tyr Val Leu Asn Ile
                95                  100                 105

Val Arg Phe Leu Glu Lys Tyr Lys Asp Ser Ala Gln Arg Asp Asp
                110                 115                 120

Met Ile Phe Glu Asp Cys Gly Asp Val Pro Ser Glu Pro Lys Glu
                125                 130                 135

Arg Gly Asp Phe Asn His Glu Arg Gly Glu Arg Lys Val Cys Arg
                140                 145                 150

Phe Lys Leu Glu Trp Leu Gly Asn Cys Ser Gly Leu Asn Asp Glu
                155                 160                 165

Thr Tyr Gly Tyr Lys Glu Gly Lys Pro Cys Ile Ile Ile Lys Leu
                170                 175                 180

Asn Arg Val Leu Gly Phe Lys Pro Lys Pro Lys Asn Glu Ser
                185                 190                 195

Leu Glu Thr Tyr Pro Val Met Lys Tyr Asn Pro Asn Val Leu Pro
                200                 205                 210

Val Gln Cys Thr Gly Lys Arg Asp Glu Asp Lys Asp Lys Val Gly
                215                 220                 225

Asn Val Glu Tyr Phe Gly Leu Gly Asn Ser Pro Gly Phe Pro Leu
                230                 235                 240

Gln Tyr Tyr Pro Tyr Tyr Gly Lys Leu Leu Gln Pro Lys Tyr Leu
                245                 250                 255

Gln Pro Leu Leu Ala Val Gln Phe Thr Asn Leu Thr Met Asp Thr
                260                 265                 270

Glu Ile Arg Ile Glu Cys Lys Ala Tyr Gly Glu Asn Ile Gly Tyr
                275                 280                 285

Ser Glu Lys Asp Arg Phe Gln Gly Arg Phe Asp Val Lys Ile Glu
                290                 295                 300

Val Lys Ser (2) INFORMATION FOR SEQ ID NO: 9:

(i) SEQUENCE CHARACTERISTICS:
        (A) LENGTH: 24 bases
        (B) TYPE: nucleic acid
        (C) STRANDEDNESS: single
        (D) TOPOLOGY: linear -continued

```
    (xi) SEQUENCE DESCRIPTION: SEQ ID NO: 9:

ATGGGGAAGG GGGTTGGACG TGAT                                    24

(2) INFORMATION FOR SEQ ID NO: 10:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO: 10:

ATAGTAGGTT TCCTTCTCCA CCCA                                    24

(2) INFORMATION FOR SEQ ID NO: 11:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO: 11:

ATGGCCCGCG GGAAAGCCAA GGAG                                    24

(2) INFORMATION FOR SEQ ID NO: 12:

(i) SEQUENCE CHARACTERISTICS:
        (A) LENGTH: 24 bases
        (B) TYPE: nucleic acid
        (C) STRANDEDNESS: single
        (D) TOPOLOGY: linear (xi) SEQUENCE DESCRIPTION: SEQ ID NO: 12:

GCTCTTAACT TCAATTTTTA CATC                                    24
```

SYSTEM AND METHOD FOR ENHANCING CARDIAC SIGNAL SENSING BY CARDIAC PACEMAKERS THROUGH GENETIC TREATMENT

This application is a continuation of application Ser. No. 08/682,433, filed Jul. 17, 1996 now abandoned.

FIELD OF THE INVENTION

The present invention relates to systems for and methods of genetically enhancing cardiac signals for use by cardiac pacemakers and, more particularly, for enhancing the signal to noise ratio of atrial P-waves for improved pacemaker sensing.

BACKGROUND OF THE INVENTION

The cardiac pacemaker is a widely used device for treating various cardiac disorders, e.g., sick sinus syndrome, "brady-tachy syndrome" and heart block. The basic function of the pacemaker is to deliver stimulus pulses to one or more of the patient's heart chambers, as and when needed, to initiate cardiac depolarizations and thus maintain a desired heart rate, or to affect improvements in cardiac output for patients in heart failure. In addition to delivering stimulus pulses, another important feature is the sensing of a patient's heartbeat signals, when they occur spontaneously, for purposes of controlling the stimulus pulse delivery. Thus, the demand pacemaker inhibits delivery of a stimulus pulse and resets the pulse generator in the event of sensing a timely spontaneous beat, i.e., a P-wave which is an atrial depolarization, or a QRS, or just R-wave, which is a ventricular depolarization. For example, an AAI mode pacemaker both paces and senses in just the atrium, and inhibits delivery of a pace pulse if a timely P-wave is sensed. The inhibit operation necessarily depends upon reliably sensing spontaneous P-waves. In a dual chamber pacemaker, both the P-wave and R-wave are sensed. As examples of dual chamber pacemakers, see U.S. Pat. Nos. 4,920,965; 4,539,991; and 4,554,921, incorporated herein by reference. A particular purpose of the dual chamber pacemaker may be to treat a block condition, where the patient's natural pacemaker is operating normally, causing timely atrial contractions, but the depolarization signal is not efficiently propagated to the ventricle so as to cause a following ventricular contraction. In such a situation, the dual chamber pacemaker is designed to sense the P-wave, and deliver a synchronized ventricular stimulus pulse, i.e., a pulse which stimulates the ventricle after a timed AV delay which approximates the AV delay of a healthy heart. It is seen that reliable sensing of the P-wave is vital to this type of dual chamber pacing.

In yet another type of pacemaker operation, the pacemaker operates in what is referred to a VDD mode, meaning that it paces only in the ventricle, but senses both P-waves and R-waves, i.e., has single chamber pacing but dual chamber sensing. The advantage of this mode is that only one lead need be positioned in the patient's heart, since no pacing pulses are delivered to the atrium. The VDD lead has the normal electrode or electrode pair at its distal end, for positioning in the ventricle; and it has a "floating" electrode (or electrode pair) proximal to the tip and positioned so that it is located in the atrium, for sensing the P-wave. See, for example, U.S. Pat. No. 5,127,694. However, since such a floating electrode is not necessarily embedded into or positioned adjacent the myocardium, the sensed P-wave is not as strong as for the case where a separate atrial lead is used, and consequently, the reliability of sensing the P-wave is even less.

Atrial sensing is additionally considered to be a significant problem because of the low P-wave amplitudes commonly available and the presence of relatively large far field QRS and other "noise" signals. It is commonly accepted that atrial P-wave amplitudes are relatively low compared to ventricular R-waves because of the differences in muscle mass near the electrodes. That is, ventricular R-waves are large because there is a large volume of myocardium around the electrode, whereas the atrial signal is small because the underlying tissue is relatively thin. Thus, for any pacing system which senses the P wave, such as an AAI pacer or any dual sense mode pacer, reliably sensing P-waves is a major problem for which improvement has long been sought.

With regard to the source of the P-wave, it is noted that it is not the muscle itself that is sensed, but the electric potentials resulting from the depolarization of several myocardial cells, i.e., a net positive ion flow into myocardial cells through specialized membrane proteins called voltage-gated ion channels, such as the sodium channels. More muscle mass means there are more membrane channels in the area adjacent to the electrodes. However, the muscle mass adjacent to the atrial electrode cannot be increased. But the P-wave could be enhanced if the number of conducting membrane channels within the adjacent muscle mass can be increased. Sodium channels are transmembrane proteins responsible for the rapid transport of $Na^+$ ions across cell membranes underlying the depolarization of the action potential in many types of cells. In particular, cardiac fast sodium channels are responsible for the fast upstroke or phase 0 of the action potential in myocardial cells. Fozzard, et al., *Circ. Res.*, 1985, 56, 475–485. Recently, a human cardiac voltage-dependent sodium channel, hH1, has been cloned, sequenced, and functionally expressed. Gellens, et al., *Proc. Natl. Acad. Sci. USA*, 1992, 89, 554–558.

Gene therapy has also recently emerged as a powerful approach to treating a variety of mammalian diseases. Direct transfer of genetic material into myocardial tissue in vivo has recently been demonstrated to be an effective method of expressing a desired protein. For example, direct myocardial transfection of plasmid DNA by direct injection into the heart of rabbits and pigs (Gal, et al., *Lab. Invest.*, 1993, 68, 18–25), as well as of rats (Acsadi, et al., *The New Biol.*, 1991, 3, 71–81), has been shown to result in expression of particular reporter gene products. In addition, direct in vivo gene transfer into myocardial cells has also been accomplished by directly injecting adenoviral vectors into the myocardium. French, et al., *Circulation*, 1994, 90, 2415–2424, and PCT Publication WO 94/11506.

Pursuant to the above, this invention provides a system and method of enhancing the cardiac pacemaker atrial and/or ventricular sensing function, i.e., enhancing the signal to noise ratio of cardiac signals, and in particular the sensed P-wave, through concurrent genetic treatment whereby the number of ion channels responsible for depolarization of the atrial or ventricular myocardial cells is increased. Applicants' invention is directed to introducing ion channel protein genetic material into myocardial cells adjacent to or closest to the position of the atrial or ventricular electrode. In any particular application, the genetic material is placed so as to provide maximum benefit for sensing P-waves, or other cardiac signals, with the pacing lead used, i.e., for an AAI pacing system, a lead which is fixated against the atrial wall.

SUMMARY OF THE INVENTION

In accordance with the above, a primary purpose of Applicants' claimed invention is to provide methods and delivery systems for enhancing cardiac pacemaker signal sensing. In a particular embodiment, the claimed invention provides methods and delivery systems for enhancing cardiac pacemaker P-wave sensing. Upon identifying a patient in which the signal to noise ratio for atrial or ventricular sensing is problematic, ion channel protein genetic material is selected such that expression of a selected ion channel protein in cells adjacent to the position of the atrial or ventricle electrode corrects or improves the signal to noise ratio for cardiac signal sensing. Preferably, expression of a selected ion channel protein can improve or correct the signal to noise ratio for cardiac signal sensing in either or both the ventricles and atria of all persons with pacemakers, especially those persons which have been diagnosed with a low signal to noise ratio for P-wave sensing. Improvement or correction of P-wave sensing can be manifested by an increase in the amplitude of the P-wave, or other characteristic of the cardiac signal, thus resulting in an increase of the signal to noise ratio of the signal sensed in the pacemaker atrial sensing channel. Delivery of the ion channel protein genetic material can be accomplished by adaptation of available pacing leads, such as, for example, AAI or DDD leads, as well as by specific modification of leads and catheters. Delivery of the genetic material may be affected by a pump or may be passive.

The ion channel protein genetic material used in the system and method of this invention comprises recombinant nucleic acid molecules comprising a nucleic acid molecule encoding the ion channel protein inserted into a delivery vehicle, such as, for example, plasmids or adenoviral vectors, and the appropriate regulatory elements. Alternatively, the ion channel protein genetic material comprises the ion channel protein itself. Expression of the desired ion channel protein from recombinant nucleic acid molecules is controlled by promoters, preferably cardiac tissue-specific promoter-enhancers, operably linked to the nucleic acid molecule encoding the ion channel protein. The conduction protein is preferably a sodium ion channel protein, such as, for example, the voltage-dependent sodium channel hH1, which is used to correct or improve the signal to noise ratio of cardiac signals, and in particular, atrial P-wave sensing. The ion channel protein genetic material is delivered to specific sites adjacent to the atrial or ventricular electrode within the heart by perfusion or injection of a therapeutically effective amount, which is that amount which corrects or improves the signal to noise ratio of the cardiac signal of the myocardial cells adjacent to the electrode. The therapeutically effective amount can be delivered to the specific site in the heart in a single dose or multiple doses, as desired.

In carrying out the treatment provided by this invention, the patient's signal to noise ratio for a particular cardiac signal, such as, for example, P-wave sensing, is first studied to determine whether such cardiac signal sensing is adequate or, rather, whether the patient presents a condition requiring adjustment, which is addressable by genetically modifying the particular cardiac signal amplitude of myocardial cells adjacent the atrial or ventricular electrode in accordance with this invention. However, in a preferred embodiment, all patients with pacemakers may receive the treatment described herein to improve the cardiac signal sensing by their pacemakers. The appropriate ion channel protein genetic material is then selected, which step includes selection of the nucleic acid molecule encoding the ion channel protein, delivery vehicle, and the appropriate regulatory elements, etc., as noted above. It is also determined what dose is indicated for treating the problematic cardiac signal to noise ratio depending upon the extent of the noise that is diagnosed, and whether follow-up treatments require implantation of an externally controllable delivery system. The determined ion channel protein genetic material is prepared, and loaded into the delivery system. The treatment is then effected by utilizing the delivery system to deliver the therapeutic dose to the patient, e.g., either injecting the material or perfusing the selected area of the heart adjacent the atrial or ventricular electrode. After this genetic treatment, the patient is paced in a standard manner, e.g., AAI pacing or dual chamber synchronous pacing which includes sensing the patient's P-waves and delivering synchronized ventricular stimulus pulses, such as in the VDD or DDD mode.

The present invention further provides a delivery system for delivering a therapeutically effective amount of a predetermined ion channel protein genetic material to an identified cardiac location adjacent the atrial or ventricular electrode, the genetic material being selected for amplifying the particular cardiac signal, such as, for example, the P-wave, from cardiac cells to which it is delivered, thus improving or correcting the cardiac signal to noise ratio received by the sensing electrode. The delivery system includes the selected genetic material contained in a reservoir, and a catheter or electrode subsystem for delivering the genetic material from the reservoir to the identified cardiac location so as to contact a plurality of cells in the proximity of the sensing electrode.

The delivery system may utilize an external reservoir for providing the genetic material, or alternately may utilize an implantable reservoir. In either embodiment, a controllable pump mechanism may be provided for transferring therapeutic doses of the genetic material from the reservoir, through a catheter or electrode, and to the selected cardiac location. The pump may be a mini or micro pump located within the delivery system. Alternatively, rather than using a pump mechanism, the ion channel protein genetic material can be passively delivered to the appropriate location adjacent the appropriate electrode. The catheter subsystem may be of a type for direct introduction into the myocardium, as with a transthoracic procedure, or, more preferably, a endocardial catheter having a distal tip portion adapted for positioning and injecting the genetic material into the myocardium from within a heart chamber. In a preferred embodiment, the catheter distal tip has a normally withdrawn helical needle, which is extendable when positioned in the vicinity of the selected site so as to be screwed into the heart. The needle is hollow and connects with the catheter lumen so as to receive the pumped genetic material; it has one or more ports located so as to effectively release the genetic material for transduction into the cardiac area adjacent the sensing electrode. In the case of an electrode subsystem, an implantable electrode is used in place of the catheter subsystem, which is able to deliver drugs, such as steroids, or other bioactive agents, such as, for example, ion channel protein genetic material. Such implantable electrodes with drug dispensing capabilities are set forth in U.S. Pat. Nos. 4,711,251, 5,458,631, 4,360,031, and 5,496,360, each of which are incorporated herein by reference. The delivery system can be used for one treatment and then removed, or can be implanted for subsequent treatments, in which latter case it is controllable by an external programmer type device. In another embodiment, the catheter or electrode subsystem may be combined with a pacing lead for sensing the patient's cardiac signals and for providing stimulus pulses.

BRIEF DESCRIPTION OF THE DRAWINGS

FIG. 3 is a schematic drawing of the distal portion of a catheter which can be used for injecting a solution carrying chosen genetic material into a patient's heart.

FIG. 4 illustrates the distal end of a catheter, having a distal portion which encloses an osmotic pump.

DESCRIPTION OF THE PREFERRED EMBODIMENTS

Figure 1:
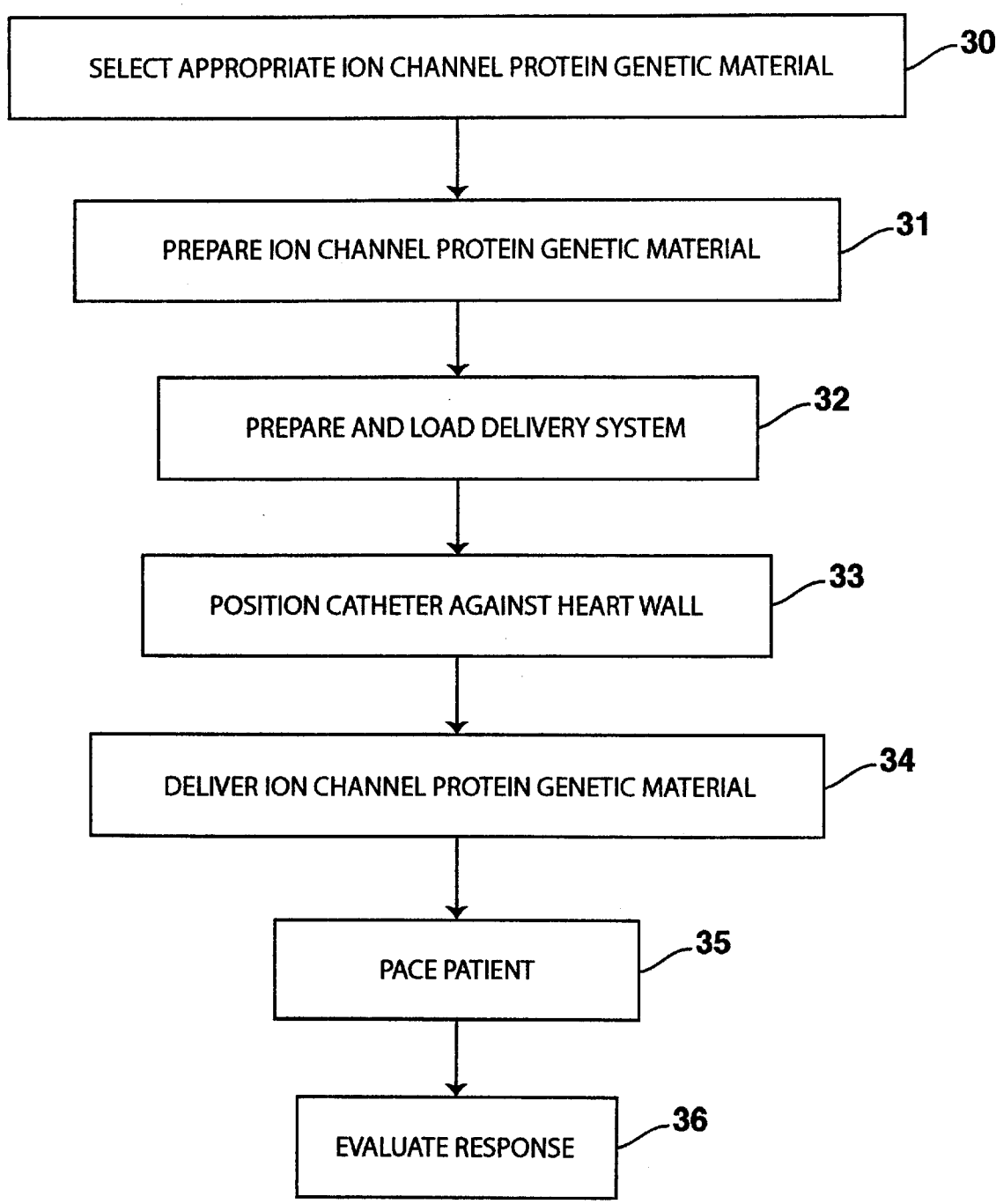
FIG. 1 is a flow diagram presenting the primary steps involved in the practice of this invention, including selecting an appropriate genetic material, positioning delivery system against the heart wall, and expressing the genetic material in an appropriate dose into the determined location.

Applicants' invention provides methods and delivery systems for correcting or improving cardiac signal sensing, especially the signal to noise ratio of the atrial P-wave, thus enhancing pacemaker sensing. A problematic signal to noise ratio for P-waves results from a naturally low amplitude P-wave generated in the atrium, noise from the ventricular QRS complex, muscle noise, noise from other sources, or a combination thereof. The signal to noise ratio is determined by routine and conventional techniques known to the skilled artisan. Once the specific problem has been identified in a particular patient, e.g., in any patient with a pacemaker or who is to receive a pacemaker, ion channel protein genetic material is selected such that expression of a selected ion channel protein corrects or improves the cardiac signal amplitude, thus improving or correcting the cardiac signal to noise ratio. The ion channel protein genetic material comprises either the ion channel protein itself or recombinant nucleic acid molecules comprising a nucleic acid molecule encoding the ion channel protein inserted into a delivery vehicle, such as, for example, plasmid, cosmid, YAC vector, viral vectors, and the like, and the appropriate regulatory elements. In preferred embodiments of the present invention, the nucleic acid molecule encoding the ion channel protein is the full length coding sequence cDNA of an ion channel protein, and is inserted into a plasmid or adenoviral vector, such as, for example, pGEM3 or pBR322, and Ad5, respectively. The regulatory elements are capable of directing expression in mammalian cells, specifically human cells. The regulatory elements include a promoter and a polyadenylation signal. Expression of the desired ion channel protein is preferably controlled by cardiac tissue-specific promoter-enhancers, operably linked to the nucleic acid molecule encoding the ion channel protein. The ion channel protein is preferably a sodium channel protein, such as, for example, the hH1 voltage-regulated sodium channel, which is used to correct or improve the cardiac signal to noise ratio. The ion channel protein genetic material is preferably delivered in a pharmaceutical composition comprising, for example, the ion channel protein genetic material in a volume of phosphate-buffered saline with 5% sucrose. In some embodiments, the ion channel protein genetic material is delivered with genetic material encoding the $Na^+/K^+$ pump, which is also inserted into an appropriate delivery vehicle. The ion channel protein genetic material may also be delivered separately or in combination with class I and class IV antiarrhythmic drugs, which have been shown to increase sodium channel mRNA expression. The ion channel protein genetic material is delivered to specific sites within the heart, adjacent to the atrial or ventricular electrode, by perfusion or injection of a therapeutically effective amount, which is that amount which corrects or improves the cardiac signal to noise ratio. Preferably, the therapeutically effective amount corrects or improves the P-wave signal to noise ratio. The therapeutically effective amount can be delivered to the specific site in the heart in single or multiple doses, as desired, using the delivery systems of the invention.

The present invention also comprises a delivery system for delivering a therapeutically effective amount of ion channel protein genetic material to a specific cardiac location, adjacent the atrial or ventricular electrode, in such a way as to enhance the amplitude of the cardiac signal, thus improving or correcting the signal to noise ratio. In a first embodiment, the delivery system basically comprises a reservoir subsystem for holding the genetic material, and a catheter subsystem in communication with the reservoir subsystem for placement of the genetic material in and around the identified cardiac location. In another embodiment, the delivery system basically comprises a reservoir subsystem for holding the genetic material, and an electrode subsystem in communication with the reservoir subsystem for placement of the genetic material in and around the identified cardiac location. As seen in the following discussion of several preferred embodiments, the reservoir subsystem and catheter subsystem or electrode subsystem may be separate, or they may be combined. Preferably the reservoir contains up to 25 ml of a genetic material for delivery to the myocardium. In some applications, only a bolus of about 0.1–10 ml, or more preferably 1–5 ml, is delivered to the targeted areas. In other applications, such as where ion channel protein is being delivered in repeated doses, 25 ml or more may be used. Also, the genetic material may be diluted in a saline solution, such as, for example, phosphate-buffered saline (PBS), the reservoir holding the diluted solution for controlled delivery. Additionally, it is to be understood that the reservoir and associated control apparatus may be either implantable or external to the body, depending upon the circumstances, e.g., whether metered doses are to be administered to the patient over a period of time, or whether the delivery of the genetic material is essentially a one time treatment.

Referring now to FIG. 1, the primary steps involved in the practice of this invention are shown in the flow diagram. The illustrated steps are performed following the initial diagnosis of a patient with a problematic P-wave signal to noise ratio, which can result from a low amplitude P-wave generated in the atrium, noise from the ventricular QRS complex, noise from other sources, or a combination thereof. Diagnosis can be accomplished, for example, by electrocardiography procedures. Preferably, the steps are performed in connection with all patients having cardiac pacemakers. As illustrated in block 30, the next step is to select the appropriate ion channel protein genetic material. This selection yields the "preselected genetic material." The ion channel protein genetic material is next prepared, as illustrated in block 31, by either inserting the nucleic acid molecules encoding the appropriate ion channel protein into a delivery vehicle with the appropriate regulatory elements, in the case of a recombinant nucleic acid molecule, or expressing the ion channel protein from an expression vector, in the case of the ion channel protein itself. As shown in block 32, the next step is to prepare and load the delivery system with a therapeutically effective amount of the ion channel protein genetic material. As illustrated in block 33, the next step comprises inserting the catheter, or other delivery subsystem, such as, for example, the electrode subsystem, into the patient's heart and positioning it against the heart wall. As shown in block 34, the next step comprises administering the therapeutically effective amount to the patient by contacting the appropriate location in the heart, adjacent to the atrial or ventricular electrode, using the delivery system described herein. An alternative method of administering the therapeutically effective amount of the ion channel protein genetic material is to directly inject the heart of the patient. The next step, shown in block 35, is to pace the patient in a standard manner, e.g., dual chamber synchronous pacing which includes sensing the patient's P-waves and delivering synchronized ventricular stimulus pulses, or AAI pacing. In accordance with this step, it may be preferable to adjust the sensitivity of the atrial or ventricular sensing channel in accordance with the observed cardiac signal amplitude. The final step 36, which is optional, is to evaluate the response of the patient to the treatment by, for example, measuring the amplitude of the cardiac signal, such as, for example, the P-wave, by conventional electrocardiographic techniques, such as, for example, by telemetry from the implanted pulse generator. The sensitivity can then be adjusted accordingly.

Figure 2:
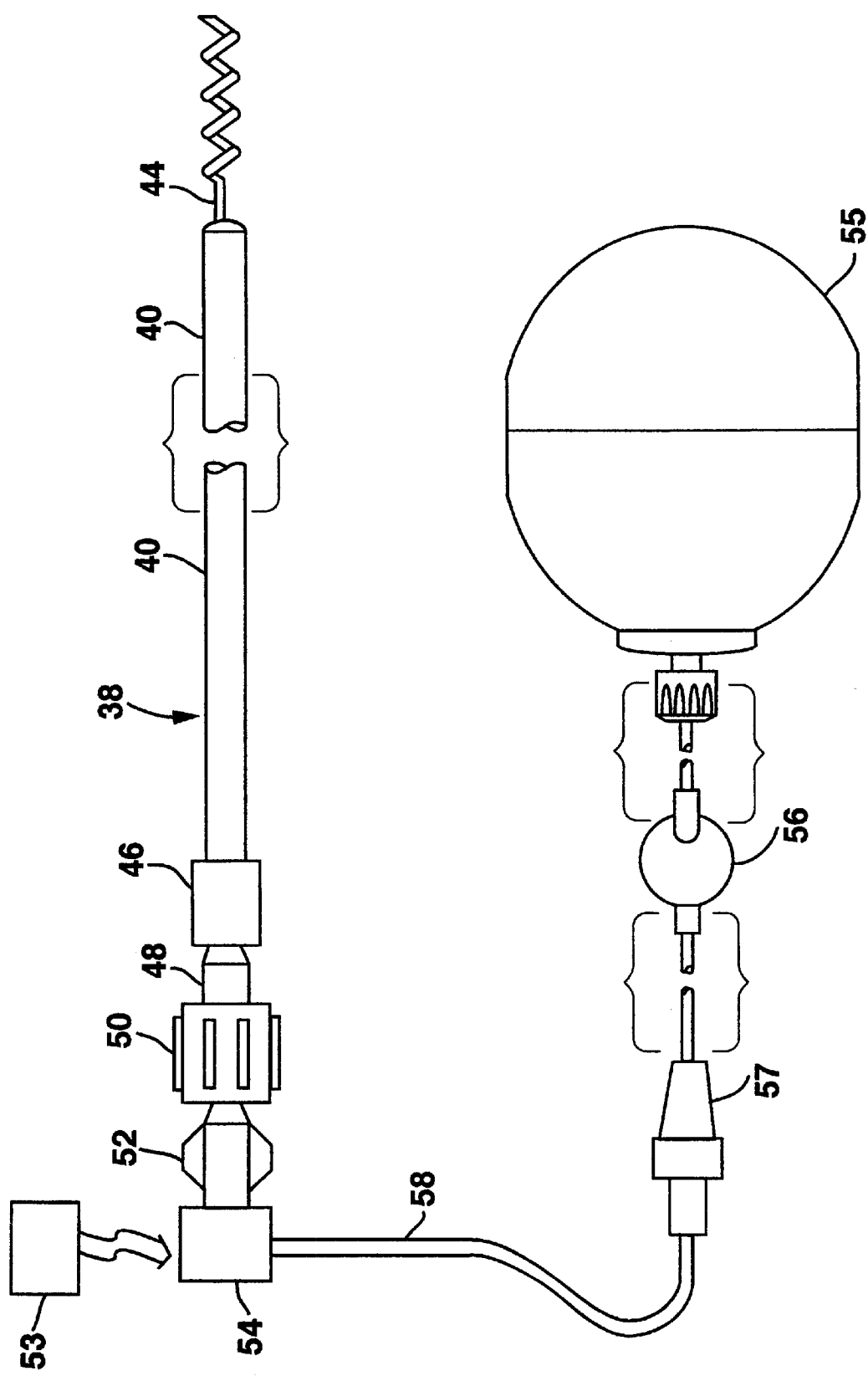
FIG. 2 is a schematic representation of a delivery system in accordance with this invention, illustrating delivery of genetic material into a patient's heart at the chosen location using a catheter subsystem.

Referring now to FIG. 2, there is shown an illustrative embodiment of a delivery system useful for certain applications of this invention, e.g., where larger amounts of genetic material alone or in solution are employed. A catheter 38, preferably a transvenous catheter, includes an elongated catheter body 40, suitably an insulative outer sheath which may be made of polyurethane, Teflon, silicone, or any other acceptable biocompatible plastic. The catheter has a standard lumen (illustrated in FIG. 3) extending therethrough for the length thereof, which communicates through to a hollow helical needle element 44, which is adapted for screwing into the patient's myocardium. The outer distal end of helical element 44 is open or porous, thus permitting genetic material in fluid form to be dispensed out of the end, as is discussed in more detail below in connection with FIG. 3. At the proximal end of the catheter, a fitting 46 is located, to which a Luer lock 48 is coupled. Luer lock 48 is coupled to the proximal end of sheath 40 and receives the lumen. A swivel mount 50 is mounted to Luer lock 48, allowing rotation of the catheter relative to Luer lock 52. Luer lock 52 in turn is coupled through control element 54 to a tube 58 which communicates with reservoir 55, suitably through flow control 57 and filter 56. Reservoir 55 holds a supply of the selected genetic material. Control elements 57 and 54 are used for adjustment of the pressure and flow rate, and may be mechanically or electronically controlled. Thus, unit 54 or 57 may be used to control either rate of delivery, or dosage size, or both. Control unit 54 may be programmed to automatically release predetermined doses on a timed basis. Further, for an implanted system, control unit 54 may be activated from an external programmer as illustrated at 53. Reference is made to international application published under the PCT, International Publication No. WO 95/05781, incorporated herein by reference, for a more detailed description of such a reservoir and catheter combination. It is to be understood that such a system is useful for this invention primarily for applications where larger fluid mounts are to be expressed, e.g., where a diluted saline solution is used to wash or perfuse a selected area.

Referring now to FIG. 3, there is shown in expanded detail a schematic of the distal end of the catheter of FIG. 2, illustrating the interconnection of the helical element 44 with the interior of the catheter. As illustrated, the helical needle 44 is provided with an internal lumen 59 which is in communication with the internal lumen 63L of the lead formed by tube 63. In this embodiment, helical element 44 may also be a pacing electrode, in which case it is formed of conductive material and welded, or otherwise fastened, to tip element 61. Tip element 61 in turn is electrically connected to coil or coils 64, 65, which extend the length of the lead and are connected to a pacemaker. An outer membrane 60 forms the outer wall of elongated catheter body 40, shown in FIG. 2. Further referring to FIG. 3, element 44 has an outlet 75 where the genetic material may be expressed, and holes or ports 76, 77, and 78 may also be utilized for providing exits for the genetic material which is supplied through lumen 59 under a suitable pressure of zero up to about one atmosphere from reservoir 55 (shown in FIG. 2) and the control elements.

In practice, a catheter 38 of the form illustrated in FIGS. 2 and 3 is advanced to the desired site for treatment, eg, adjacent the site where the sensing electrode is to be positioned. The catheter may be guided to the indicated location by being passed down a steerable or guidable catheter having an accommodating lumen, for example as disclosed in U.S. Pat. No. 5,030,204; or by means of a fixed configuration guide catheter such as illustrated in U.S. Pat. No. 5,104,393. Alternately, the catheter may be advanced to the desired location within the heart by means of a deflectable stylet, as disclosed in PCT Patent Application WO 93/04724, published Mar. 18, 1993, or by a deflectable guide wire as disclosed in U.S. Pat. No. 5,060,660. In yet another embodiment, the helical element 44 may be ordinarily retracted within a sheath at the time of guiding the catheter into the patient's heart, and extended for screwing into the heart by use of a stylet. Such extensible helical arrangements are well known in the pacing art, and are commercially available.

It is to be understood that other forms of the reservoir subsystems and catheter subsystems are within the scope of this invention. Reservoir embodiments include, for example, drug dispensing irrigatable electrodes, such as those described in U.S. Pat. No. 4,360,031; electrically controllable, non-occluding, body implanting drug delivery system, such as those described in U.S. Pat. No. 5,041,107; implantable drug infusion reservoir such as those described in U.S. Pat. No. 5,176,641; medication delivery devices such as those described in U.S. Pat. No. 5,443,450; infusion pumps, such as SYNCHROMED7 made by Medtronic, Inc.; and osmotic pumps, such as those made by Alza.

Referring now to FIG. 4, there is shown, by way of illustration, another embodiment of a delivery system having a combined catheter and reservoir, useful for applications involving delivery of a relatively small bolus of genetic material, e.g., 1–5 ml. FIG. 4 illustrates the distal end of a catheter, having a distal portion 70 which encloses an osmotic pump. See U.S. Pat. No. 4,711,251, assigned to Medtronic, Inc., incorporated herein by reference. The pump includes an inner chamber 68 and an outer chamber 66, which chambers are separated by an impermeable membrane 67. A semi-permeable outer membrane 72 forms the outer wall of chamber 66. The tubular portion 74 of the helical member connects to lumen 74L within inner chamber 68. A conductor 80, which runs the length of the catheter, extends into the inner chamber 68 and connects with extension 74E as shown at 74C to provide electrical contact through to element 44, in an application which the element 44 is used as a pacing electrode. An insulating cover 86 encompasses the conductor 80 from the point of contact with the semi-permeable outer membrane 72 distally. A seal 79 is provided at the point where the conductor passes through outer membrane 72 and inner membrane 67. An end cap 73, which may be integral with outer membrane 72 closes the chamber. Alternately, end cap 73 may be constructed to elute a predetermined medication, such as, for example, steroids. Steroids, such as dexamethasone sodium phosphate, beclamethasone, and the like, are used to control inflammatory processes.

In this arrangement, prior to inserting the catheter distal end into the patient's heart, the inner chamber 68 is charged with the genetic material which is to be dispensed into the myocardium. This may be done, for example, by simply inserting a micro needle through end cap 73, and inserting the desired bolus of genetic material into chamber 68. After the chamber 68 is filled and the is catheter is implanted, body fluids will enter chamber 66 through membrane 72 to impart a pressure on the inner chamber 68 via the impermeable membrane 67. This results in a dispensing of the genetic material stored within chamber 68 through the lumen 74L of extension 74E and through the outlet 75 of the helical element 44. Although the preferred needle or element 44 is helical, additional configurations of needles or elements can also be used as known to those skilled in the art.

Still referring now to FIG. 4, there is illustrated another embodiment of a catheter tip useful for delivering a small bolus of the selected genetic material. In this embodiment, the bolus of material is stored within the hollow interior of distal needle 44, i.e., the interior is the reservoir. The interior reservoir is maintained sealed by use of a soluble material which is normally solid, but which dissolves when subjected to body fluids for a period of time. An example of such material is mannitol. Plugs or globules 81–85 of mannitol are illustrated (by dashed lines) in place to block the two ends of element 44, as well as the ports 76, 77, 78. This may be combined with an osmotic pump, as described in connection with FIG. 3, where the outer chamber is filled with a saline solution which forces the genetic material out of the ports of element 44. Another alternate embodiment, not shown, is to use a stylet which inserted through to the distal end of the catheter, to push a piston which aids in expressing the genetic material into the myocardial cells. Alternatively, the piston can be driven by a micro pump. In another embodiment, the genetic material contacts the myocardial cells by passive delivery.

Figure 5A:
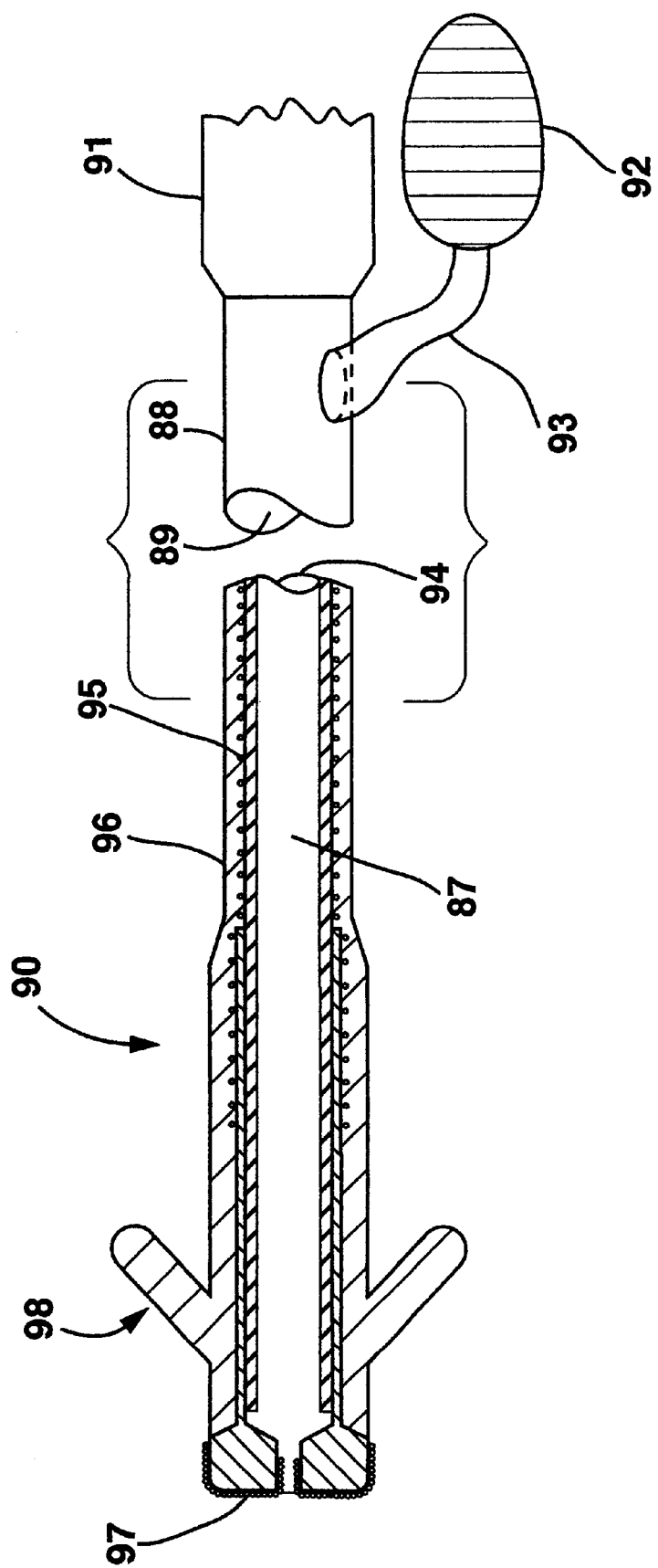
FIG. 5A is a schematic representation of a delivery system in accordance with this invention, having a combined catheter and pacing lead, with a separate pump.

Referring now to FIG. 5A, there is shown, by way of illustration, another embodiment of an implantable delivery system comprising a combined pacing lead and delivery catheter, hereinafter referred to simply as a catheter. In this embodiment, the catheter 90 is combined with a pacemaker or pulse generator (not shown) and a source of genetic material such as illustrated by pump 92 which is suitably implanted near the pacemaker. The proximal end 91 of the catheter is connected to the pacemaker in the standard fashion. The genetic material is delivered through connecting tube 93 to a proximal section 88 of the catheter, communicating with lengthwise catheter lumen illustrated at 89. Alternately, the pacemaker head may contain a reservoir and micropump, for providing delivery of the genetic material directly to the lumen 89. The main length of the catheter has an outside sheath of biocompatible insulating material 96, and at least one conductor coil 95 which communicates electrically from the pacemaker to electrode 97 at the distal tip of the catheter. The catheter further comprises an axially positioned polymeric cannula 94, having lumen 87, through at least a portion of the catheter length and positioned within coil 95, which provides an inner surface for the catheter lumen. The cannula terminates at the distal end of the catheter, just proximal to the tip portion of electrode 97, which is illustrated as having an outer porous surface. Electrode 97 has a central opening, shown covered with the porous electrode material, through which genetic material can pass when the catheter is positioned in the patient. As shown, conductor coil 95 is electrically connected to electrode 97, and connects pace pulses and sensed cardiac signals between the pacemaker and the electrode. Of course, for a bipolar embodiment, the lead/catheter 90 carries a second electrode (not shown), suitably a ring electrode just proximal to electrode 97. Also, as illustrated, a fixation mechanism such as tines 98 are employed for fixing or anchoring the distal tip to the heart wall of the patient.

In one embodiment, pump 92 is suitably an osmotic minipump, which pumps fluid contained within through tube 93, into catheter portion 88 and through the lumens 89, 87 to the tip electrode 97. As mentioned previously, the reservoir and pump may alternately be mounted in the pacemaker device itself. In either instance, the genetic material is delivered under very minimal pressure from the reservoir through the lumen of the catheter to the electrode, where it is passed through the electrode central channel to contact myocardial cells. In yet another embodiment, the lumen portion 87 provided by the cannula is utilized as the reservoir. In this embodiment, delivery may either be passive, or with the aid of a micropump (not shown). The genetic material can be preloaded into the cannula, or it can be inserted by a needle just before the catheter is introduced and positioned with the patient.

Figure 5B:
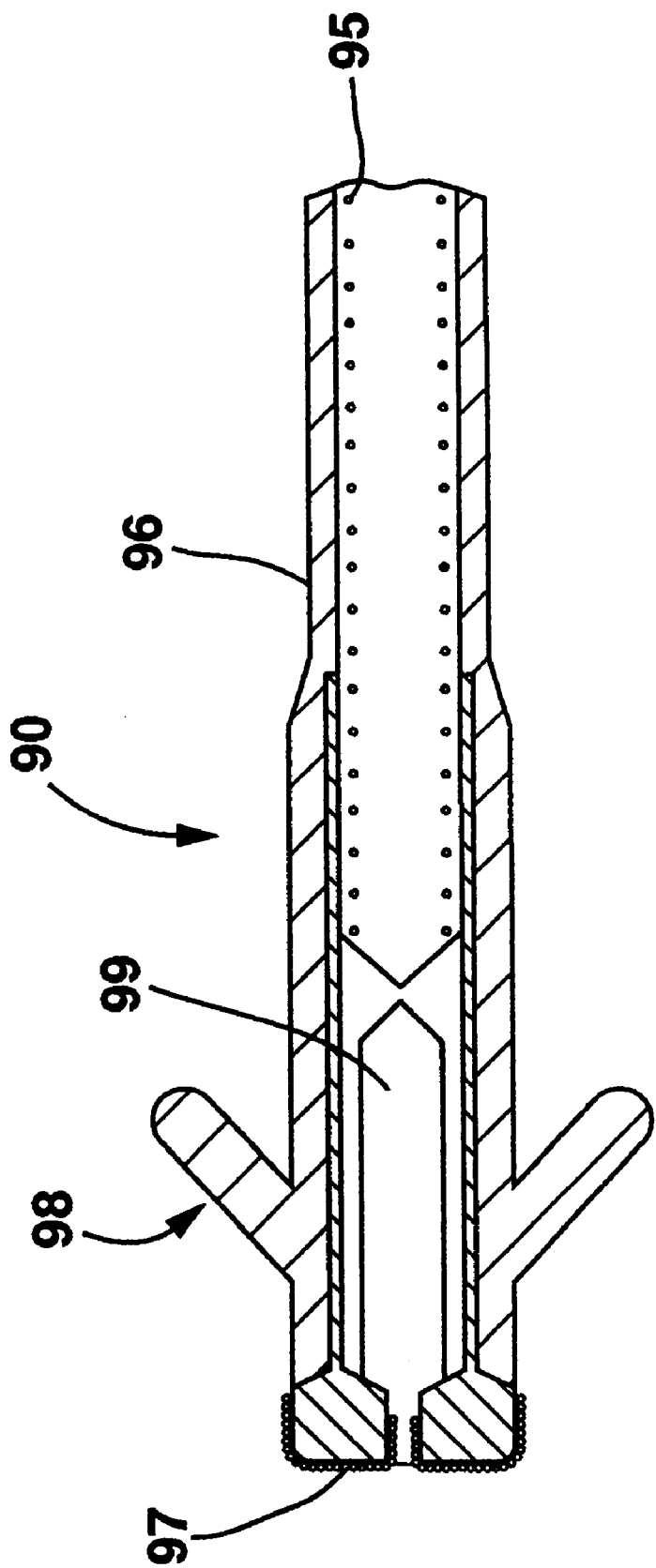
FIG. 5B is another embodiment of a combined pacing lead and delivery catheter having a reservoir located at the distal end of the catheter.

In another embodiment, as illustrated in FIG. 5B, a chamber 99 is provided just proximal from eluting electrode 97, and serves as the reservoir of the genetic material. Insulating material 96 is formed from a self-sealing material such that it may be pierced with a needle, or the like, and reseal itself, thus allowing introduction of the genetic material into the chamber prior to implantation. Alternately, insulating material 96 can contain a port (not shown) through which the needle inserts the genetic material. In this embodiment, delivery of the material is without a pump, i.e., passive, the material draining slowly through the microporous portion of electrode 97.

The above described delivery systems can be used, for example, in methods of pacing and enhancing the detectability of sensed cardiac signals. A supply of a genetic material of the class having the property of increasing the expression of ion channels in cardiac cells to which it is delivered is selected. A transvenous catheter, having proximal and distal ends and a pacing electrode at the distal end, is introduced into the patient. The distal end of the catheter is positioned against the patient's heart wall and the genetic material is delivered through the catheter and out of the distal end, to the cardiac cells adjacent the pacing electrode, thereby enhancing cardiac signals produced by the cells. Normal cardiac pacing is carried out with the pacemaker and connected catheter implanted in the patient.

Although a transvenous form of delivery system is preferred, it is to be understood that the invention can employ other methods and devices. For example, a small bolus of selected genetic material can be loaded into a micro-syringe, e.g., a 100 µl Hamilton syringe, and applied directly from the outside of the heart.

As used herein, the phrase ▒cardiac signal▒ refers to any cardiac signal that is detectable and includes, but is not limited to, the P-wave.

As used herein, the phrase "signal to noise ratio" refers to the ratio of the amplitude of the cardiac signal, such as, for example, the P-wave, to the amplitude of the "noise." In addition, the signal to noise ratio can be measured for other cardiac signals as well. Sources of "noise" include, but are not limited to, the QRS complex and muscle noise. It is desirable to establish a high signal to noise ratio, i.e., a signal to noise ratio of greater than 1:1 for unipolar leads and greater than 3:1 for bipolar leads. It is even more preferred to establish a signal to noise ratio greater than 10:1.

As used herein, the phrase "ion channel protein genetic material" refers to recombinant nucleic acid molecules encoding an ion channel protein or, alternatively, an ion channel protein itself, which is used in the methods and delivery systems of the invention. For chronic treatment, or long term treatment, the ion channel protein genetic material will be in the form of recombinant nucleic acid molecules encoding the ion channel protein. In contrast, for acute treatment, or short term treatment, the ion channel protein genetic material will be in the form of the ion channel proteins themselves.

A "recombinant nucleic acid molecule", as used herein, is comprised of an isolated ion channel protein-encoding nucleotide sequence inserted into a delivery vehicle. Regulatory elements, such as the promoter and polyadenylation signal, are operably linked to the nucleotide sequence encoding the ion channel protein, whereby the protein is capable of being produced when the recombinant nucleic acid molecule is introduced into a cell.

The nucleic acid molecules encoding the ion channel proteins are prepared synthetically or, preferably, from isolated nucleic acid molecules, as described below. A nucleic acid is "isolated" when purified away from other cellular constituents, such as, for example, other cellular nucleic acids or proteins, by standard techniques known to those of ordinary skill in the art. The coding region of the nucleic acid molecule encoding the ion channel protein can encode a full length gene product or a subfragment thereof, or a novel mutated or fusion sequence. The protein coding sequence can be a sequence endogenous to the target cell, or exogenous to the target cell. The promoter, with which the coding sequence is operably associated, may or may not be one that normally is associated with the coding sequence.

The nucleic acid molecule encoding the ion channel protein is inserted into an appropriate delivery vehicle, such as, for example, an expression plasmid, cosmid, YAC vector, and the like. Almost any delivery vehicle can be used for introducing nucleic acids into the cardiovascular system, including, for example, recombinant vectors, such as one based on adenovirus serotype 5, Ad5, as set forth in French, et al., *Circulation*, 1994, 90, 2414–2424, which is incorporated herein by reference. An additional protocol for adenovirus-mediated gene transfer to cardiac cells is set forth in WO 94/11506, Johns, *J. Clin. Invest.*, 1995, 96, 1152–1158, and in Barr, et al., *Gene Ther.*, 1994, 1, 51–58, both of which are incorporated herein by reference. Other recombinant vectors include, for example, plasmid DNA vectors, such as one derived from pGEM3 or pBR322, as set forth in Acsadi, et al., *The New Biol.*, 1991, 3, 71–81, and Gal, et al., *Lab. Invest.*, 1993, 68, 18–25, both of which are incorporated herein by reference, cDNA-containing liposomes, artificial viruses, nanoparticles, and the like. It is also contemplated that ion channel proteins be injected directly into the myocardium.

The regulatory elements of the recombinant nucleic acid molecules of the invention are capable of directing expression in mammalian cells, specifically human cells. The regulatory elements include a promoter and a polyadenylation signal. In addition, other elements, such as a Kozak region, may also be included in the recombinant nucleic acid molecule. Examples of polyadenylation signals useful to practice the present invention include, but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, can be used.

The promoters useful in constructing the recombinant nucleic acid molecules of the invention may be constitutive or inducible. A constitutive promoter is expressed under all conditions of cell growth. Exemplary constitutive promoters include the promoters for the following genes: hypoxanthine phosphoribosyl transferase (HPRT), adenosine deaminase, pyruvate kinase, β-actin, human myosin, human hemoglobin, human muscle creatine, and others. In addition, many viral promoters function constitutively in eukaryotic cells, and include, but are not limited to, the early and late promoters of SV40, the Mouse Mammary Tumor Virus (MMTV) promoter, the long terminal repeats (LTRs) of Maloney leukemia virus, Human Immunodeficiency Virus (HIV), Cytomegalovirus (CMV) immediate early promoter, Epstein Barr Virus (EBV), Rous Sarcoma Virus (RSV), and other retroviruses, and the thymidine kinase promoter of herpes simplex virus. Other promoters are known to those of ordinary skill in the art.

Inducible promoters are expressed in the presence of an inducing agent. For example, the metallothionein promoter is induced to promote (increase) transcription in the presence of certain metal ions. Other inducible promoters are known to those of ordinary skill in the art.

Promoters and polyadenylation signals used must be functional within the cells of the mammal. In order to maximize protein production, regulatory sequences may be selected which are well suited for gene expression in the cardiac cells into which the recombinant nucleic acid molecule is administered. For example, the promoter is preferably a cardiac tissue-specific promoter-enhancer, such as, for example, cardiac isoform troponin C (cTNC) promoter. Parmacek, et al., *J. Biol. Chem.*, 1990, 265, 15970–15976, and Parmacek, et al., *Mol. Cell Biol.*, 1992, 12, 1967–1976. In addition, codons may be selected which are most efficiently transcribed in the cell. One having ordinary skill in the art can produce recombinant nucleic acid molecules which are functional in the cardiac cells.

Genetic material can be introduced into a cell or "contacted" by a cell by, for example, transfection or transduction procedures. Transfection refers to the acquisition by a cell of new genetic material by incorporation of added nucleic acid molecules. Transfection can occur by physical or chemical methods. Many transfection techniques are known to those of ordinary skill in the art including: calcium phosphate DNA co-precipitation; DEAE-dextran DNA transfection; electroporation; naked plasmid adsorption, and cationic liposome-mediated transfection. Transduction refers to the process of transferring nucleic acid into a cell using a DNA or RNA virus. Suitable viral vectors for use as transducing agents include, but are not limited to, retroviral vectors, adeno associated viral vectors, vaccinia viruses, and Semliki Forest virus vectors.

Treatment of cells, or contacting cells, with recombinant nucleic acid molecules can take place in vivo or ex vivo. For ex vivo treatment, cells are isolated from an animal (preferably a human), transformed (i.e., transduced or transfected in vitro) with a delivery vehicle containing a nucleic acid molecule encoding an ion channel protein, and then administered to a recipient. Procedures for removing cells from mammals are well known to those of ordinary skill in the art. In addition to cells, tissue or the whole or parts of organs may be removed, treated ex vivo and then returned to the patient. Thus, cells, tissue or organs may be cultured, bathed, perfused and the like under conditions for introducing the recombinant nucleic acid molecules of the invention into the desired cells.

For in vivo treatment, cells of an animal, preferably a mammal and most preferably a human, are transformed in vivo with a recombinant nucleic acid molecule of the invention. The in vivo treatment may involve systemic intravenous treatment with a recombinant nucleic acid molecule, local internal treatment with a recombinant nucleic acid molecule, such as by localized perfusion or topical treatment, and the like. When performing in vivo administration of the recombinant nucleic acid molecule, the preferred delivery vehicles are based on noncytopathic eukaryotic viruses in which nonessential or complementable genes have been replaced with the nucleic acid sequence of interest. Such noncytopathic viruses include retroviruses, the life cycle of which involves reverse transcription of genomic viral RNA into DNA with subsequent proviral integration into host cellular DNA. Retroviruses have recently been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M. "Gene Transfer and Expression, a Laboratory Manual", W. H. Freeman Co., New York (1990) and Murry, E. J. e.d. "Methods in Molecular Biology", Vol. 7, Humana Press, Inc., Clifton, N.J. (1991).

A preferred virus for contacting cells in certain applications, such as in in vivo applications, is the adeno-associated virus, a double-stranded DNA virus. The adeno-associated virus can be engineered to be replication deficient and is capable of infecting a wide range of cell types and species. It further has advantages such as heat and lipid solvent stability, high transduction frequencies in cells of diverse lineages, including hemopoietic cells, and lack of superinfection inhibition thus allowing multiple series of transductions. Recent reports indicate that the adeno-associated virus can also function in an extrachromosomal fashion.

In preferred embodiments of the present invention, the recombinant nucleic acid molecules comprising nucleic acid molecules encoding the ion channel proteins, or, in the alternative, the ion channel proteins, are delivered to cardiac cells adjacent the atrial or ventricular electrode, or both, using the delivery systems set forth above. Alternatively, the ion channel protein genetic material is delivered to the cardiac cells by direct injection.

In preferred embodiments of the present invention, the nucleic acid molecules encoding the ion channel proteins comprise the full length coding sequence cDNA of an ion channel protein. Preferably, the ion channel proteins are sodium channel proteins; more preferably, the ion channel protein is the voltage-regulated sodium channel hH1. Such a nucleic acid molecule is described in the Gellens, et al., Proc. Natl. Acad. Sci. USA, 1992, 89, 554–558, and White, et al., Mol. Pharmacol., 1991, 39, 604–608 references, both of which are incorporated herein by reference, which contain the full length amino acid sequence and cDNA sequence, respectively.

Introduction of the ion channel-encoding nucleic acid molecules or the ion channel proteins to cardiac cells adjacent the atrial or ventricular electrode will result in increased expression of sodium channels, producing a larger cardiac signal, such as, for example, P-wave, and thus, an improved or corrected signal to noise ratio. Nucleic acid molecules comprising nucleotide sequences encoding hH1 sodium channel are isolated and purified according to the methods set forth in Gellens, et al., Proc. Natl. Acad. Sci. USA, 1992, 89, 554–558, and White, et al., Mol. Pharmacol., 1991, 39, 604–608. The nucleic acid and protein sequences of hH1 sodium channel are set forth in SEQ ID NO:1 and SEQ ID NO:2, respectively. It is contemplated that nucleic acid molecules comprising nucleotide sequences that are preferably at least 70% homologous, more preferably at least 80% homologous, and most preferably at least 90% homologous to the ion channel nucleotide sequences described in SEQ ID NO:1 can also be used.

It is understood that minor modifications of nucleotide sequence or the primary amino acid sequence may result in proteins which have substantially equivalent or enhanced activity as compared to the ion channel proteins exemplified herein. These modifications may be deliberate, as through site-directed mutagenesis, or may be accidental such as through mutations in hosts which produce the ion channel proteins. A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein can result from deletions, additions, or substitutions. A "deletion" is defined as a polypeptide in which one or more internal amino acid residues are absent as compared to the native sequence. An "addition" is defined as a polypeptide which has one or more additional internal amino acid residues as compared to the wild type protein. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar and/or aromatic. It is generally preferred that encoded peptides differing from the native form contain substituted codons for amino acids which are from the same group as that of the amino acid replaced. Thus, in general, the basic amino acids Lys, Arg, and Histidine are interchangeable; the acidic amino acids Asp and Glu are interchangeable; the neutral polar amino acids Ser, Thr, Cys, Gln, and Asn are interchangeable; the nonpolar aliphatic acids Gly, Ala, Val, Ile, and Leu are conservative with respect to each other (but because of size, Gly and Ala are more closely related and Val, Ile and Leu are more closely related), and the aromatic amino acids Phe, Trp, and Tyr are interchangeable.

While Pro is a nonpolar neutral amino acid, it represents difficulties because of its effects on conformation, and substitutions by or for Pro are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by codons for amino acids from different classes may also be useful.

Once the nucleic acid molecules encoding the ion channel proteins are isolated and purified according to the methods described above, recombinant nucleic acid molecules are prepared in which the desired ion channel nucleic acid molecule is incorporated into a delivery vehicle by methods known to those skilled in the art, as taught in, for example, Sambrook et al., *Molecular Cloning: A Laboratory Manual*, Second Ed. Cold Spring Harbor Press (1989). Preferred delivery vehicles include, for example, plasmids (Acsadi, et al., *The New Biol.*, 1991, 3, 71–81, and Gal, et al., *Lab. Invest.*, 1993, 68, 18–25, both of which are incorporated herein by reference) and adenovirus (WO 94/11506, Johns, *J. Clin. Invest.*, 1995, 96, 1152–1158, and in Barr, et al., *Gene Ther.*, 1994, 1, 51–58, each of which are incorporated herein by reference). The nucleic acid molecules encoding ion channel proteins, or ion channel proteins produced therefrom, are delivered to the cardiac cells adjacent to the atrial electrode by the delivery systems of the present invention. Thus, such delivery systems of the present invention are used to contact the cardiac cells adjacent the atrial electrode with recombinant nucleic acid molecules encoding an ion channel protein, or ion channel proteins.

Where the ion channel protein genetic material is in the form of ion channel proteins, such proteins can be prepared in large quantities by using various standard expression systems known to those skilled in the art. Sambrook et al., *Molecular Cloning: A Laboratory Manual*, Second Ed. Cold Spring Harbor Press (1989), pp. 16.1–16.55, incorporated herein by reference.

The recombinant nucleic acid molecules or ion channel proteins are preferably delivered in a pharmaceutical composition. Such pharmaceutical compositions can include, for example, the recombinant nucleic acid molecule or protein in a volume of phosphate-buffered saline with 5% sucrose. In other embodiments of the invention, the recombinant nucleic acid molecule or protein is delivered with suitable pharmaceutical carriers, such as those described in the most recent edition of *Remington's Pharmaceutical Sciences*, A. Osol, a standard reference text in this field. The recombinant nucleic acid molecule or protein is delivered in a therapeutically effective amount. Such amount is determined experimentally and is that amount which either improves or corrects the P-wave signal to noise ratio by enhancing the P-wave amplitude as a result of the increased expression of sodium channels in the cardiac cells adjacent the atrial or ventricular electrode. The amount of recombinant nucleic acid molecule or protein is preferably between 0.01 $\mu$g and 100 mg, more preferably between 0.1 $\mu$g and 10 mg, more preferably between 1 $\mu$g and 1 mg, and most preferably between 10 $\mu$g and 100 $\mu$g. A single therapeutically effective amount is referred to as a bolus. Where adenovirus vectors are used, the amount of recombinant nucleic acid molecule is preferably between $10^7$ plaque forming units (pfu) and $10^{15}$ pfu, more preferably between $10^8$ pfu and $10^{14}$ pfu, and most preferably between $10^9$ pfu and $10^{12}$ pfu. A single therapeutically effective amount of ion channel protein genetic material is referred to as a bolus. In some embodiments of the present invention, the delivery of the recombinant nucleic acid molecules or proteins is combined with steroid elution, such as with dexamethasone sodium phosphate, beclamethasone, and the like, to control inflammatory processes.

In some embodiments of the invention, it may be preferred to administer, in addition to ion channel protein genetic material, delivery vehicle encoding the $Na^+/K^+$ pump. The $Na^+/K^+$ pump acts to discharge $Na^+$ ions from the myocardial cells that have accumulated as a result of the introduction of the ion channel protein genetic material. This treatment can be optional, as determined by the skilled practitioner. cDNA encoding the alpha and beta subunits of the human $Na^+/K^+$ pump are set forth in Kawakami, et al., *J. Biochem.*, 1986, 100, 389–397, and Kawakami, et al., *Nuc. Acids Res.*, 1986, 14, 2833–2844, both of which are incorporated herein by reference. The nucleic acid and amino acid sequences for the alpha subunit are set forth in SEQ ID NO:5 and SEQ ID NO:6, respectively. The nucleic acid and amino acid sequences for the beta subunit are set forth in SEQ ID NO:7 and SEQ ID NO:8, respectively. The delivery vehicles for the pump subunits can be constructed from cDNA libraries in the same manner as set forth for hH1, except that the forward primer 5'-ATGGGGAAGGGGGTTGGACGTGAT-3' (SEQ ID NO:9) and reverse primer 5'-ATAGTAGGTTTCCTTCTCCACCCA-3' (SEQ ID NO:10) for the alpha subunit, and the forward primer 5'-ATGGCCCGCGGGAAAGCCAAGGAG-3' (SEQ ID NO:11) and reverse primer 5'-GCTCTTAACTTCAATTTTTACATC-3' (SEQ ID NO:12) for the beta subunit are used. It is understood that other primers can be used in addition to those set forth herein, as is well known to the skilled artisan. A therapeutically effective amount of the genetic material encoding the $Na^+/K^+$ pump is delivered to the myocardial cells using the delivery systems described herein. The therapeutically effective amount is determined by the practitioner, and depends upon the results achieved with the ion channel protein genetic material.

In preferred embodiments of the invention, the recombinant nucleic acid molecules encoding the ion channel proteins is delivered with class I and/or class IV antiarrhythmic drugs, such as, for example, verapamil, mexiletine, and the like, or combinations thereof. These drugs may be delivered subcutaneously, intravenously, injected in the immediate vicinity of the atrial electrode, or as determined by the skilled artisan. These drugs may be delivered by one injection, or in multiple injections. The amount of antiarrhythmic drugs depends upon the age, weight, sex, and other characteristics of the patient, and is determined empirically by the skilled artisan. Class I and/or class IV antiarrhythmic drugs have been shown to enhance sodium ion channel expression in mammals. Duff, et al., *Mol. Pharmacol.*, 1992, 42, 570–574, and Taouis, et al., *J. Clin. Invest.*, 1991, 88, 375–378, both of which are incorporated herein by reference.

The following examples are meant to be exemplary of the preferred embodiments of the invention and are not meant to be limiting.

EXAMPLES

Example 1

Isolation and Purification of Nucleic Acid Molecule Encoding hH1

Nucleic acid molecules encoding hH1 are isolated and purified according to general methods well known to those skilled in the art, and in particular, by the method set forth in Gellens, et al., *Proc. Natl. Acad. Sci. USA,* 1992, 89, 554–558, incorporated herein by reference. Briefly, a size selected and random-primed adult human cardiac cDNA library constructed in λZAPII (Stratagene) is screened with cDNA probes corresponding to nucleotides 1–4385 and 5424–7076 derived from the rat muscle TTX-I isoform (rSkM2), as set forth in Kallen, et al., *Neuron,* 1990, 4, 233–242, incorporated herein by reference. Hybridizations are performed at 42EC for 18 hours in 50% formamide, 5×SSPE, 5×Denhardt's solution, 0.1% SDS/salmon sperm DNA, random primed $^{32}$P-labeled probe. Filters are washed with 6×standard saline citrate, 0.1% SDS at 65EC. Plaque purified clones are rescued as pBluescript phagemids and sequenced as described in Kallen, et al., *Neuron,* 1990, 4, 233–242. A full-length hH1 construct is made in pBluescript by sequential ligation of S14 EcoR1-Sac II (nt +1 to +252), C75 Sac II-KpnI (nt +253 to +4377), and C92 KpnI-EcoR1 (nt +4378 to +8491) fragments and the full length insert is moved into a modified pSP64T vector, as set forth in White, et al., *Mol. Pharmacol.,* 1991, 39, 604–608, incorporated herein by reference. Nucleotides −151 to −8 of the 5' untranslated region are deleted from the construct using exonuclease III and mung bean nuclease, as set forth in White, et al., *Mol. Pharmacol.,* 1991, 39, 604–608.

Alternatively, cDNA for hH1 may be prepared from fresh cardiac tissue. Briefly, total cellular RNA is isolated and purified (Chomczynsky, et al., *Anal. Biochem.,* 1987, 162, 156–159) from heart tissue, obtained from cardiac transplantation donors, or from salvaged tissue, and selected for poly(A) RNA (Sambrook et al., *Molecular Cloning: A Laboratory Manual,* Second Ed. Cold Spring Harbor Press (1989), pp. 7.26–7.29). cDNA corresponding to the hH1 sodium channel protein is prepared from the poly(A) cardiac RNA by reverse transcription using a GENEAMP™ PCR kit (Perkin Elmer Cetus, Norwalk, Conn.), or the like, using random hexamers according to the manufacturer's instructions. The specific hH1 nucleic acid molecules are amplified by the polymerase chain reaction (PCR), also using the GENEAMP™ PCR kit, or the like, using forward and reverse primers specific for hH1 according to the manufacturer's instructions. For example, the forward primer for cloning hH1 is preferably 5'-ATGGCAAACTTCCTATTACCTCGG-3' (SEQ ID NO:3), and the reverse primer is 5'-CACGATGGACTCACGGTCCCTGTC-3' (SEQ ID NO:4). It is understood that additional primers can be used for amplification as determined by those skilled in the art. These primers may be preceded at the 5' terminus by nucleotide sequences containing endonuclease restriction sites for easy incorporation into vectors. The specific ion channel nucleic acid molecules can also be amplified by PCR from human genomic DNA (Stratagene, San Diego, Calif.). After cutting the PCR products with the appropriate restriction endonuclease(s), the PCR products are purified by phenol:chloroform extractions, or using commercial purification kits, such as, for example, MAGIC™ Minipreps DNA Purification System (Promega, Madison, Wis.). The specific nucleotide sequence of the PCR products is determined by conventional DNA sequencing procedures, and the identity of the PCR products confirmed by comparison to the published sequences for the ion channel proteins.

Example 2

Insertion of Ion Channel cDNA into Delivery Vehicles

Preferably, ion channel cDNA is inserted into either plasmid or adenoviral vectors. Plasmid vectors include for example, pGEM3 or pBR322, as set forth in Acsadi, et al., *The New Biol.,* 1991, 3, 71–81, and Gal, et al., *Lab. Invest.,* 1993, 68, 18–25. Adenoviral vectors include for example, adenovirus serotype 5, Ads, as set forth in French, et al., *Circulation,* 1994, 90, 2414–2424, and Johns, *J. Clin. Invest.,* 1995, 96, 1152–1158.

Preferably, the primers used to amplify the ion channel nucleic acid molecules are designed with unique endonuclease restriction sites located at the 5' terminus. In the absence of such design, polylinker arms, containing unique restriction sites, can be ligated thereto. After cutting the purified PCR products with the appropriate restriction endonuclease(s), the plasmid vector, comprising a polylinker, is also cut with the same restriction endonuclease (s), affording the ion channel nucleic acid molecule a site at which to ligate. In a similar manner, recombinant adenovirus (Gluzman, et al., in *Eukaryotic Viral Vectors,* Gluzman, ed., Cold Spring Harbor Press, 1982, pp.187–192, French, et al., *Circulation,* 1994, 90, 2414–2424, and Johns, *J. Clin. Invest.,* 1995, 96, 1152–1158) containing ion channel cDNA molecules are prepared in accordance with standard techniques well known to those skilled in the art.

It is contemplated that variations of the above-described invention may be constructed that are consistent with the spirit of the invention.

What is claimed is:

1. A delivery system for delivering a predetermined genetic material or protein to myocardial cells of a selected location of a patient's heart, comprising:
   a sensor for locating an area of inadequate P-wave production in the heart of a patient; and
   a delivery means for delivering a supply of said genetic material or protein to said selected location in said patients heart wherein said genetic material is selected from the group consisting of DNA encoding an ion channel protein, RNA encoding an ion channel protein, and an ion channel protein.

2. The delivery system of claim 1, wherein said delivery means further comprises a catheter.

3. The delivery system of claim 1, wherein said catheter is an endocardial catheter.

4. The delivery system of claim 2, wherein said delivery means comprises a hollow helical screw-in element.

5. The delivery system of claim 1, wherein said supply of genetic material is provided as a bolus to said selected location.

6. The delivery system of claim 1, wherein the delivery means forms part of the sensor.

7. The delivery system of claim 1, where the delivery means is not part of the sensor.

8. The deivery system of claim 1, wherein said selected genetic material is a recombinant nucleic acid molecule encoding the ion channel protein.

9. The delivery system of claim 8, wherein said ion channel protein is a sodium channel protein.

10. The delivery system of claim 9, wherein sodium channel protein is hH1.

11. The delivery system of claim 1, wherein said genetic material or protein increases the amplitude of the cardiac signal of said patient's heart.

12. An implantable delivery system for delivering doses of predetermined genetic material or protein to myocardial cells in a chosen location of a patient's heart, comprising:
   a sensor for detecting cardiac signals from said chosen location;
   a supply of genetic material or protein selected from group consisting of DNA encoding an ion channel protein, RNA encoding an ion channel protein, and an ion channel protein; and
   an implantable delivery means for delivering said genetic material or protein to said chosen location.

13. The implantable delivery system as described in claim 12, further comprising a control means for controlling operation of said delivery means.

14. The implantable delivery system of claim 12, wherein said controlling means controls the rate of delivery of said doses.

15. The implantable delivery system of claim 12, wherein said control means comprises automatic means for automatically initiating delivery of said genetic material.

16. The delivery system of claim 12, wherein said genetic material or protein increases the amplitude of the cardiac signal of said patient's heart.

17. The delivery system of claim 12, wherein said supply of genetic material is provided as a bolus to said selected location.

18. The delivery system of claim 12, wherein said selected general material is a recombinant nucleic acid molecule encoding the ion channel protein.

19. The delivery system of claim 18, wherein said ion channel protein is a sodium channel protein.

20. The delivery system of claim 19, wherein said sodium channel protein is hH1.

21. An implantable delivery system for delivering predetermined genetic material or protein to cardiac cells adjacent to a pacing electrode positioned in the heart of a patient, comprising:

a supply of genetic material or protein selected from the group consisting of DNA encoding an ion channel protein, RNA encoding an ion channel protein, and an ion channel protein;

a pacing electrode adapted to be positioned in the heart of a patient; and a delivery means for delivering said genetic material or protein to said cardiac cells adjacent to said pacing electrode positioned in the heart of a patient.

22. The implantable delivery system of claim 21 wherein the pacing electrode is positioned against the inner wall of a patient's heart.

23. The implantable delivery system of claim 21, wherein said delivery means forms part of said pacing electrode.

24. The system as described in claim 21, further comprises a control means for controlling operation of said delivery means to deliver said genetic material or protein.

25. The implantable delivery system of claim 21, further comprising a control means for controlling the rate of delivery of said doses.

26. The implantable delivery system of claim 21, wherein said control means comprises automatic means for initiating delivery of said genetic material.

27. The delivery system of claim 21, wherein said genetic material or protein increases the amplitude of the cardiac signal of said patient's heart.

28. The delivery system of claim 21, wherein said delivery means comprises a hollow helical screw-in element.

29. The delivery system of claim 21, wherein the delivery means forms part of the sensor.

30. The delivery system of claim 21, wherein said supply of genetic material is provided as a bolus to said selected location.

31. The delivery system of claim 21, wherein said selected genetic material is a recombinant nucleic acid molecule encoding the ion channel protein.

32. The delivery system of claim 31, wherein said ion channel protein is a sodium channel protein.

33. The delivery system of claim 32, wherein said sodium channel protein is hH1.

* * * * *